United States Patent
Kitagawa et al.

(10) Patent No.: US 10,593,428 B2
(45) Date of Patent: Mar. 17, 2020

(54) DIAGNOSIS SUPPORT APPARATUS AND METHOD, AND NON-TRANSITORY COMPUTER READABLE MEDIUM

(71) Applicant: FUJIFILM Corporation, Tokyo (JP)

(72) Inventors: Yusuke Kitagawa, Kanagawa (JP); Shoji Kanada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1029 days.

(21) Appl. No.: 15/054,150

(22) Filed: Feb. 26, 2016

(65) Prior Publication Data
US 2016/0253467 A1    Sep. 1, 2016

(30) Foreign Application Priority Data
Feb. 27, 2015 (JP) ................. 2015-039540

(51) Int. Cl.
*G16H 50/20* (2018.01)
*G16H 40/63* (2018.01)
(Continued)

(52) U.S. Cl.
CPC ............. *G16H 50/20* (2018.01); *G06F 19/00* (2013.01); *G16H 40/63* (2018.01); *G16H 50/50* (2018.01);
(Continued)

(58) Field of Classification Search
CPC ........... A61N 1/08; G06F 17/30; G06F 19/30; G06F 19/32; G06F 19/321; G06F 19/324;
(Continued)

(56) References Cited

U.S. PATENT DOCUMENTS 5,583,758 A * 12/1996 McIlroy ................ G06F 19/325
705/2
5,786,816 A * 7/1998 Macrae ................ G06F 19/325
128/920
(Continued)

FOREIGN PATENT DOCUMENTS

| JP | 2010200840 | 9/2010 |
|---|---|---|
| JP | 2011118543 | 6/2011 |
| JP | 2013-149265 | 8/2013 |

OTHER PUBLICATIONS

"Office Action of Japan Counterpart Application," with machine English translation thereof, dated Feb. 14, 2018, p. 1-p. 9.

*Primary Examiner* — Jonathan Durant
*Assistant Examiner* — Gregory D. Moseley
(74) *Attorney, Agent, or Firm* — JCIPRNET

(57) ABSTRACT

A diagnosis support apparatus for diagnosis of a patient body includes a diagnosis support device, which determines diagnosis support information for use in reference for the diagnosis by running a diagnosis support program according to plural input list items related to medical care data of the patient body. An evaluator compares a contribution value of contribution of the input list items to determining the diagnosis support information with a predetermined threshold, to generate contribution information related to at least one large contribution list item of which the contribution value is equal to or more than the threshold. A display panel displays the diagnosis support information and the contribution information, so that system visibility can be high. Preferably, the input list items include at least one of list items related to medication, a vital sign, a diagnostic test and imaging.

15 Claims, 20 Drawing Sheets

(51) Int. Cl.
    *G16H 50/50*         (2018.01)
    *A61B 5/00*          (2006.01)
    *A61B 5/0205*      (2006.01)
    *G06F 19/00*       (2018.01)

(52) U.S. Cl.
    CPC ......... *A61B 5/02055* (2013.01); *A61B 5/7275* (2013.01); *A61B 5/743* (2013.01); *A61B 5/7435* (2013.01)

(58) Field of Classification Search
    CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06F 19/00; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00; A61B 5/02055; A61B 5/7435; A61B 5/743; A61B 5/7275
    See application file for complete search history.

(56)           References Cited

U.S. PATENT DOCUMENTS

| | | |
|---|---|---|
| 8,880,455 B2 | 11/2014 | Kawagishi et al. |
| 9,436,915 B2 | 9/2016 | Kawagishi et al. |
| 2016/0357925 A1 | 12/2016 | Kawagishi et al. |

\* cited by examiner

FIG. 8

| SYMPTOM (SYMPTOM ID) | LIST ITEM | | DIAGNOSIS SUPPORT PGM (PGM ID) |
|---|---|---|---|
| SYMPTOM A | MEDICATION | DRUG A<br>DRUG B | PGM A1 (SUGGESTED DRUG)<br>PGM A2 (SIMILAR CASE)<br>PGM A3 (SIMILAR IMAGE)<br>PGM A4 (MEDICATION SIM)<br>⋮ |
| | VITAL SIGN | BLOOD PRESSURE (UPPER)<br>BLOOD PRESSURE (LOWER)<br>⋮ | |
| | DIAGNOSTIC TEST | BIOCHEMICAL A<br>BIOCHEMICAL B<br>⋮ | |
| | IMAGING | CT | |
| SYMPTOM B | MEDICATION | DRUG A<br>DRUG C | PGM B1 (SUGGESTED DRUG)<br>PGM B2 (SIMILAR CASE)<br>PGM B3 (SIMILAR IMAGE)<br>PGM B4 (MEDICATION SIM)<br>⋮ |
| | VITAL SIGN | BLOOD PRESSURE (UPPER)<br>BLOOD PRESSURE (LOWER)<br>⋮ | |
| | DIAGNOSTIC TEST | BIOCHEMICAL E<br>BIOCHEMICAL F<br>⋮ | |
| | IMAGING | ULTRASOUND | |
| COMPLEX DISEASE A-B | MEDICATION | DRUG A<br>DRUG B<br>DRUG C | PGM AB1 (SUGGESTED DRUG)<br>PGM AB2 (SIMILAR CASE)<br>PGM AB3 (SIMILAR IMAGE)<br>PGM AB4 (MEDICATION SIM)<br>⋮ |
| | VITAL SIGN | BLOOD PRESSURE (UPPER)<br>BLOOD PRESSURE (LOWER)<br>⋮ | |
| | DIAGNOSTIC TEST | BIOCHEMICAL A<br>BIOCHEMICAL B<br>BIOCHEMICAL E<br>BIOCHEMICAL F<br>BIOCHEMICAL G<br>⋮ | |
| | IMAGING | CT<br>ULTRASOUND | |

F I G . 14
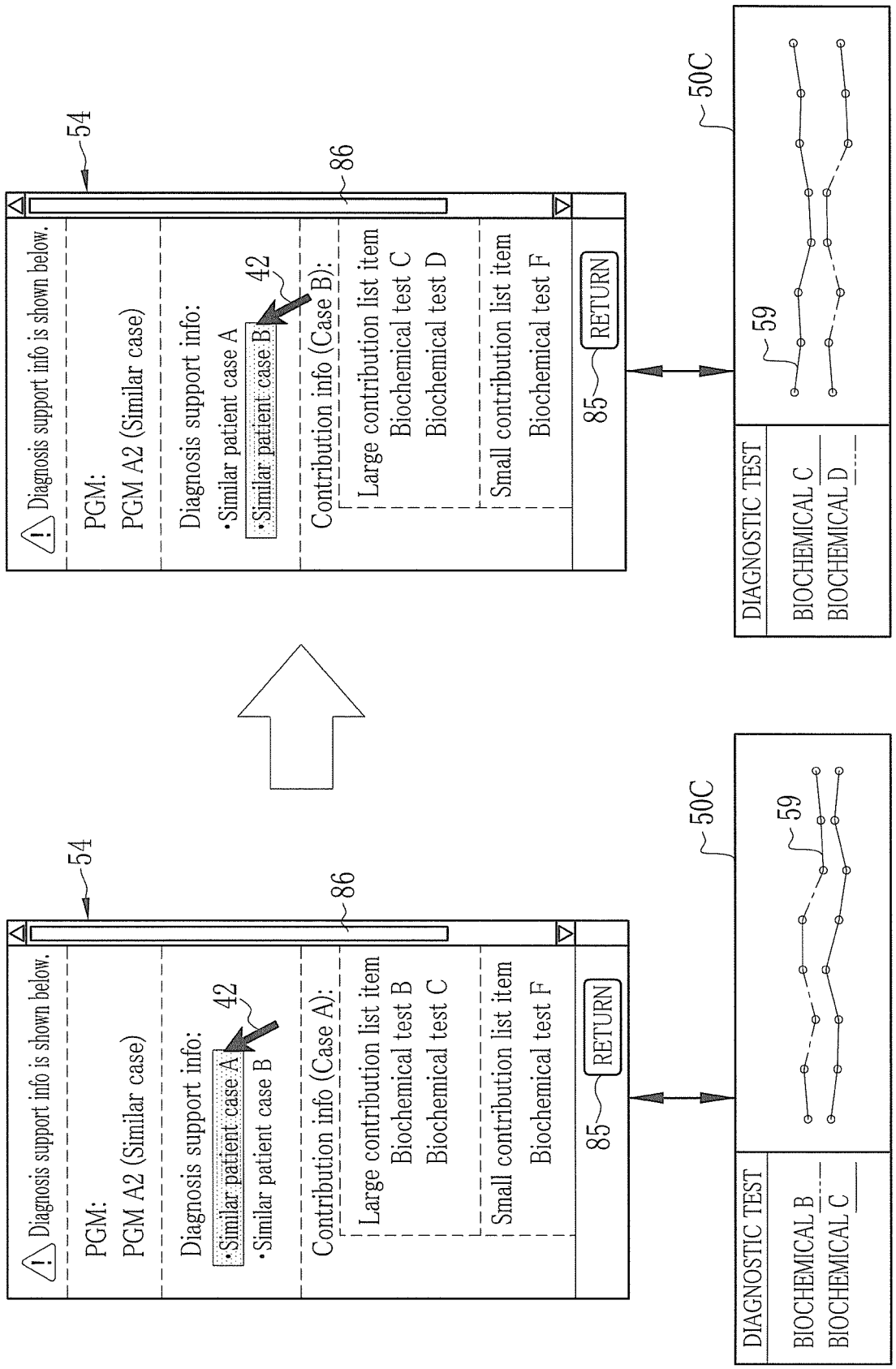

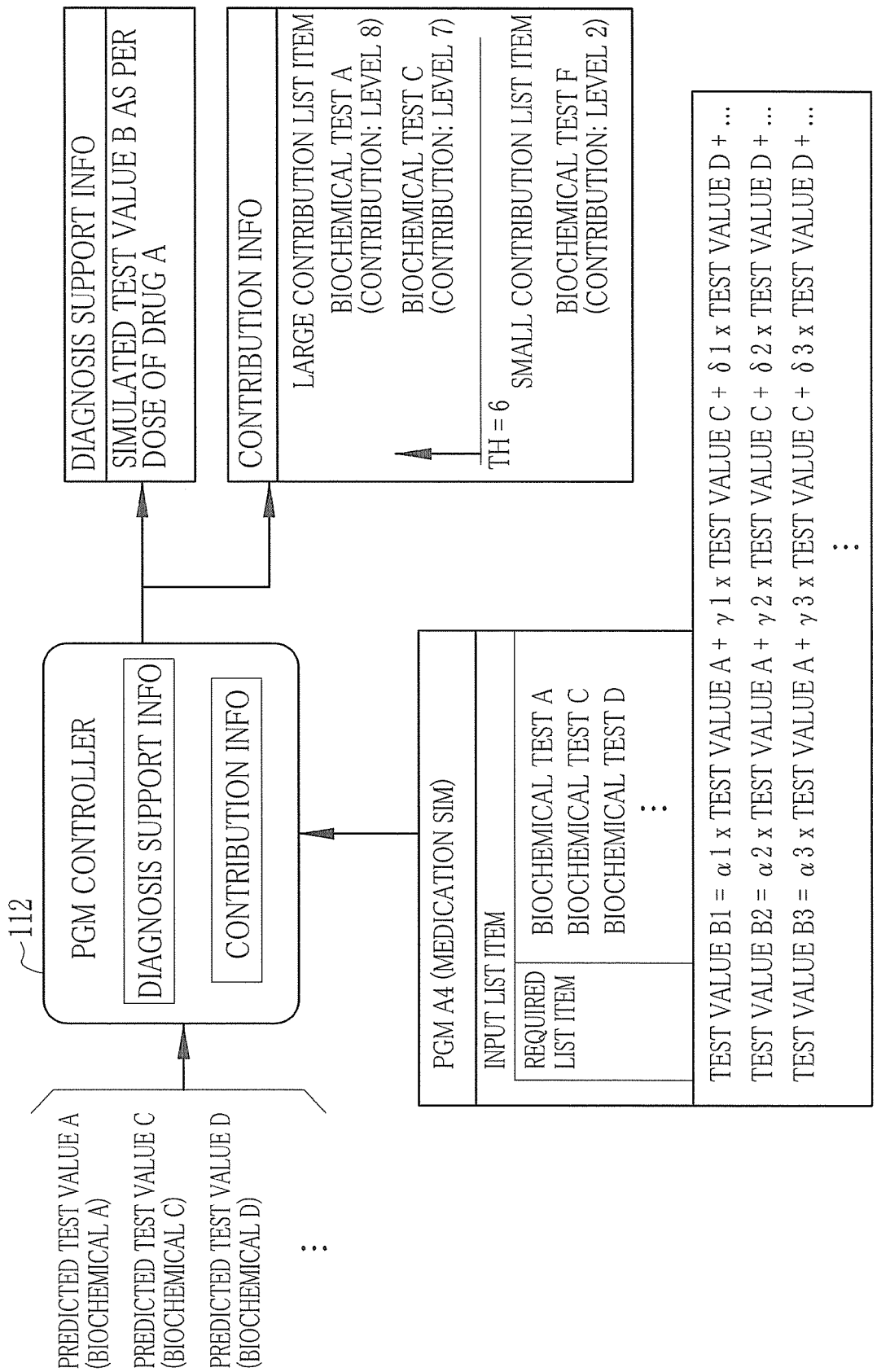

DIAGNOSIS SUPPORT APPARATUS AND METHOD, AND NON-TRANSITORY COMPUTER READABLE MEDIUM

CROSS-REFERENCE TO RELATED APPLICATION

This application claims priority under 35 USC 119 from Japanese Patent Application No. 2015-039540, filed 27 Feb. 2015, the disclosure of which is incorporated by reference herein.

BACKGROUND OF THE INVENTION

1. Field of the Invention

The present invention relates to a diagnosis support apparatus and method, and non-transitory computer readable medium. More particularly, the present invention relates to a diagnosis support apparatus and method for outputting diagnosis support information, and in which reliability in determining the diagnostic support information can be clarified, and a non-transitory computer readable medium.

2. Description Related to the Prior Art

A diagnosis support program for medical use is known, in which medical care data of a patient (patient body) is collected and analyzed to output diagnosis support information, for aid in a doctor's diagnosis and medical care for the patient. JP-A 2013-149265 discloses a diagnosis support apparatus which receives a diagnostic image as the medical care data, and determines the diagnosis support information by use of the diagnosis support program. Also, a difference is obtained arithmetically by the diagnosis support apparatus between the diagnosis support information from the diagnosis support program and information of an image reading report produced by a doctor viewing and interpreting the diagnostic image, so that a display panel displays information of the difference.

The diagnosis support information according to the diagnosis support program is of great concern today in the field of medical diagnostic techniques in the rapid development of information technology. For example, big data of the medical care data can be handled and processed in the diagnosis support program of new development, so that it will be possible easily to obtain the diagnosis support information of great aid, for example, suggestion of a pharmaceutical drug according to genetic information. Further use of the diagnosis support program will encourage innovation of advanced procedures in the field of medicine.

However, a problem remains in slowness of spreading the utilization of the diagnosis support program for the diagnosis support information between doctors. A main reason for the problem is that reliability of the diagnosis support information is unclear in view of proper medical care. In general, the diagnosis support program is developed by programmers or developers and completed after supervision of doctors or medical professionals as a specialist of the medicine. However, each of the users or individual doctors cannot observe the entire processing of the diagnosis support program with combinations of logic flows or processes of the determination. In short, system visibility of the diagnosis support program is low.

Let a plurality of list items be input for the medical care data in the diagnosis support program. Arithmetic processing to determine the diagnosis support information is based on part of the list items with higher relevancy. However, a process (logic flow) of the arithmetic processing is hidden (invisible) and unknown to users as a black box. A doctor does not find the process in the black box with clarity and cannot utilize the diagnosis support program with reliability. Although utilization of the diagnosis support program should be encouraged, there is no known technique of maintaining the reliability of the diagnosis support program from a point of view of doctors.

It is impossible in the diagnosis support apparatus of JP-A 2013-149265 to solve the above problem, because the document only discloses display of the difference between the diagnosis support information from the diagnosis support program and information of a result of the check-up or diagnosis of a doctor.

SUMMARY OF THE INVENTION

In view of the foregoing problems, an object of the present invention is to provide a diagnosis support apparatus and method for outputting diagnosis support information, and in which reliability in determining the diagnostic support information can be clarified, and a non-transitory computer readable medium.

In order to achieve the above and other objects and advantages of this invention, a diagnosis support apparatus for diagnosis of a patient body includes a diagnosis support information acquisition unit acquires diagnosis support information determined for use in reference for the diagnosis by running a diagnosis support program according to plural input list items related to medical care data of the patient body. A contribution information acquisition unit acquires contribution information, generated by comparing a contribution value of contribution of the input list items to determining the diagnosis support information with a predetermined threshold, and related to at least one large contribution list item of which the contribution value is equal to or more than the threshold. An information output device provides the diagnosis support information and the contribution information.

Preferably, the information output device performs display processing to display the diagnosis support information and the contribution information in an information page for displaying the medical care data.

Preferably, the evaluator acquires information of a small contribution list item of which a contribution value to the determined diagnosis support information is less than the threshold among the input list items. The information output device displays the large contribution list item and the small contribution list item distinctly from one another.

Preferably, the information page displays the large contribution list item in a display sequence of highness of the contribution value.

Preferably, in case one of the at least one large contribution list item is specified in the information page, the medical care data corresponding to the specified large contribution list item is displayed.

Preferably, in case plural sets of the diagnosis support information are displayed in the information page and one of the sets is specified, then the large contribution list item related to the specified set is displayed.

Preferably, the medical care data corresponding to the input list items is time sequential data for changes in a value with time, and the information page displays information of a period of the time sequential data used for determining the diagnosis support information.

Preferably, the information of the period is displayed with an emphasis in correspondence with the large contribution list item.

Preferably, assuming that there is an unused list item unused in determining the diagnosis support information among the input list items, information of the unused list item is displayed in the information page.

Preferably, the unused list item is additionally specifiable as an input list item for subsequently determining the diagnosis support information.

Preferably, the diagnosis support program produces the diagnosis support information by simulation with a polynomial equation, and the large contribution list item is a list item corresponding to at least one of plural explanatory variables in the polynomial equation.

Preferably, a function of the diagnosis support program includes a function of at least one of suggesting a drug, searching a similar patient case, searching a similar image, and simulating administration of a drug.

Preferably, the input list items include at least one of list items related to medication, a vital sign, a diagnostic test and imaging.

Also, a diagnosis support method for diagnosis of a patient body is provided, and includes a step of acquiring diagnosis support information determined for use in reference for the diagnosis by running a diagnosis support program according to plural input list items related to medical care data of the patient body. Contribution information is acquired, the contribution information being generated by comparing a contribution value of contribution of the input list items to determining the diagnosis support information with a predetermined threshold, and related to at least one large contribution list item of which the contribution value is equal to or more than the threshold. The diagnosis support information and the contribution information is provided.

Also, a non-transitory computer readable medium for storing a computer-executable program enabling execution of computer instructions to perform operations for diagnosis support for diagnosis of a patient body is provided. The operations include acquiring diagnosis support information determined for use in reference for the diagnosis according to plural input list items related to medical care data of the patient body. The operations include acquiring contribution information, generated by comparing a contribution value of contribution of the input list items to determining the diagnosis support information with a predetermined threshold, and related to at least one large contribution list item of which the contribution value is equal to or more than the threshold. The operations include providing the diagnosis support information and the contribution information.

Consequently, reliability in determining the diagnostic support information can be clarified with system visibility, because contribution information of a large contribution list item can be displayed together with diagnosis support information.

BRIEF DESCRIPTION OF THE DRAWINGS

The above objects and advantages of the present invention will become more apparent from the following detailed description when read in connection with the accompanying drawings, in which:

FIG. 8 is a mapping table illustrating a symptom list;

FIG. 14 is a screen view illustrating a relationship between the diagnosis support information and medical care data;

FIG. 20 is a data chart illustrating a diagnosis support program for simulating drug administration.

DETAILED DESCRIPTION OF THE PREFERRED EMBODIMENT(S) OF THE PRESENT INVENTION

First Embodiment

Figure 1:
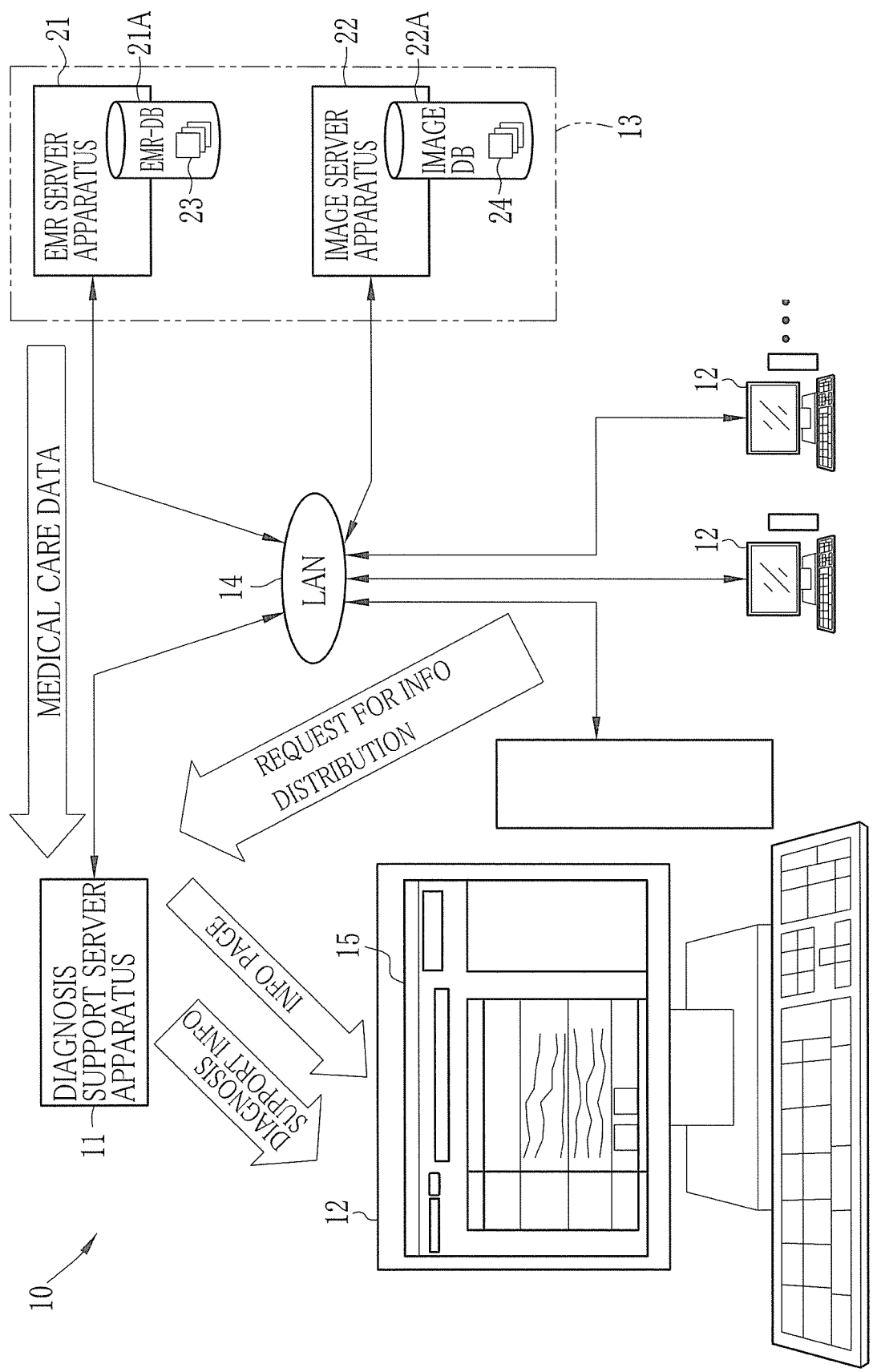
FIG. 1 is a block diagram schematically illustrating a diagnosis support system.

In FIG. 1, a diagnosis support system 10 or computer aided diagnosis system (CAD) or clinical decision support system (CDSS) is a computer system for managing and utilizing medical care data in a hospital facility, which can be a hospital, clinic, sanatorium and the like. The diagnosis support system 10 includes a diagnosis support server apparatus 11, a client terminal apparatus 12 and a server cluster 13. A LAN 14 (local area network) or other network interconnects those components in a communicable manner inside a site of the hospital facility.

The diagnosis support server apparatus 11 functions as a diagnosis support apparatus of the invention. A request for information distribution from the client terminal apparatus 12 is received by the diagnosis support server apparatus 11. The diagnosis support server apparatus 11 upon receiving the request transmits a request to the server cluster 13 for acquiring medical care data obtained in the entire period of medical care of a patient (patient body). The diagnosis support server apparatus 11 acquires the medical care data from the server cluster 13 according to the request for the acquisition, and creates an information page 15 for medical care data (in FIG. 6) according to the medical care data. The diagnosis support server apparatus 11 outputs the information page 15 to the client terminal apparatus 12 as a requester of the request.

Figure 11:
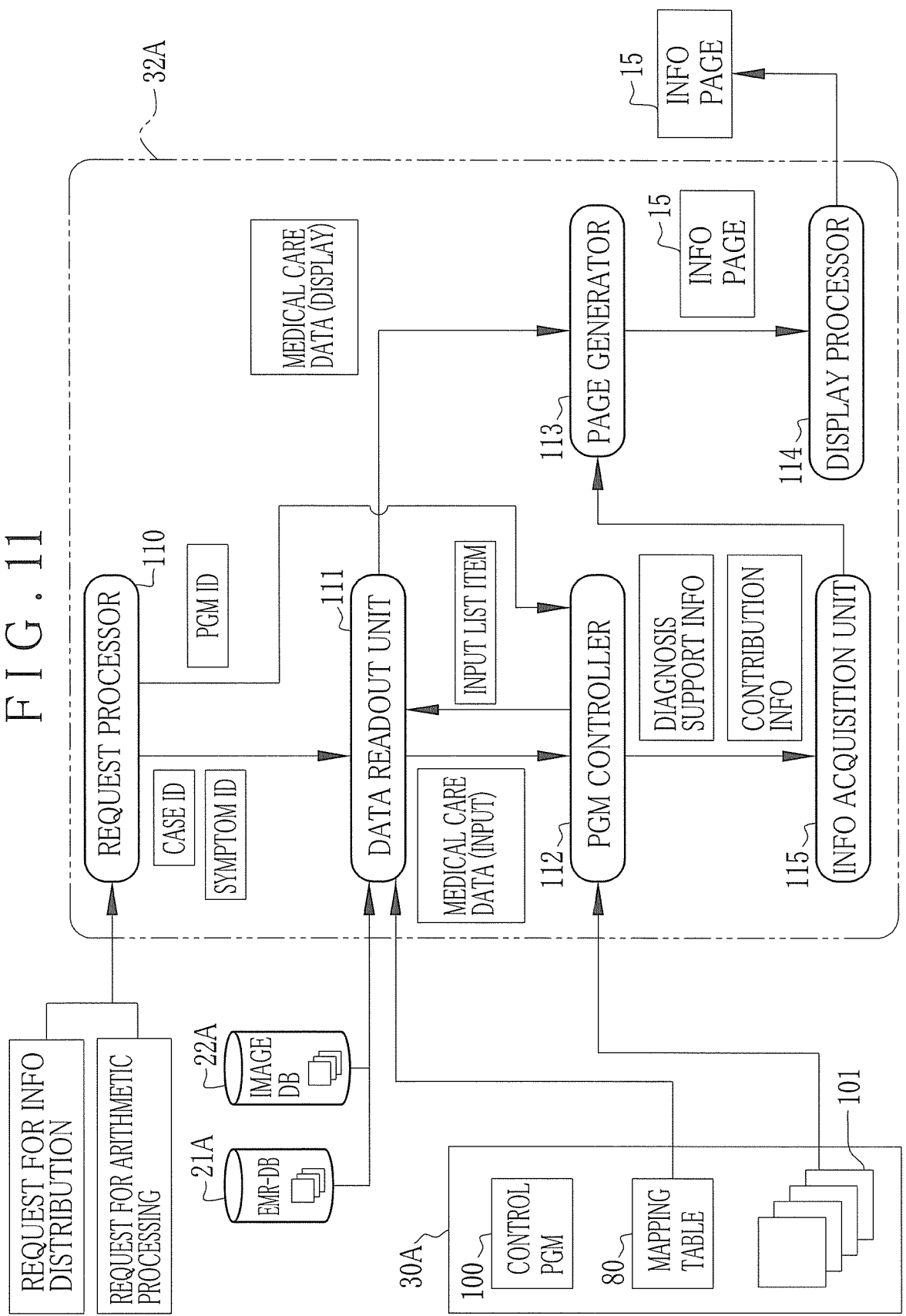
FIG. 11 is a block diagram schematically illustrating circuit devices in the diagnosis support server apparatus.

Also, a plurality of diagnosis support computer-executable programs 101 of FIG. 11 are executable in the diagnosis support server apparatus 11, which outputs diagnosis support information as a result of performing tasks from input data or medical care data in the diagnosis support programs 101. The diagnosis support information is reference information for diagnosing the patient body, and processed with the information page 15 in display processing, and transmitted to the client terminal apparatus 12. See FIG. 9.

The client terminal apparatus 12 is disposed in each one of hospital departments, such departments as internal medicine, surgery, otolaryngology and ophthalmology for medical care, and is manually operated by a doctor or user. The client terminal apparatus 12 transmits a request for the information distribution of medical care data to the server cluster 13, and transmits a request for the information distribution of the information page 15 to the diagnosis support server apparatus 11. The client terminal apparatus 12 displays the information page 15 and the medical care data distributed by the diagnosis support server apparatus 11 or the server cluster 13 according to the request for the information distribution, for use in medical care of professionals. The client terminal apparatus 12 is a viewer terminal apparatus for viewing the information page 15 and the medical care data.

The diagnosis support server apparatus 11 distributes the information page 15 to the client terminal apparatus 12 in a format of XML data for web distribution created according to the XML (Extensible Markup Language) as a markup language. The client terminal apparatus 12 performs display processing to display the information page 15 on the web browser according to the XML data. Also, it is possible to use another data description language instead of the XML, such as JSON (JavaScript Object Notation) and the like, JavaScript being a trade name.

The server cluster 13 searches and reads out medical care data according to the request for information distribution from the client terminal apparatus 12, and transmits the searched medical care data to the client terminal apparatus 12. Also, the server cluster 13 searches and reads out medical care data according to the request for acquisition from the diagnosis support server apparatus 11, and transmits the searched medical care data to the diagnosis support server apparatus 11.

The server cluster 13 includes an EMR server apparatus 21 and an image server apparatus 22. An EMR database 21A or DB is combined with the EMR server apparatus 21. EMRs 23 (electronic medical records) are stored in the EMR database 21A. Data in the EMRs 23 include progress data, test data, measurement values of vital signs, and treatment data. Examples of the progress data include results of questionnaire and check-up. Examples of the test data are test values of a blood test, biochemical test and other diagnostic test, and of electroencephalography (EEG) and other physiological test. Examples of the vital signs are a heart rate, respiratory rate, body temperature and blood pressure. Examples of the treatment data include intervention, surgery, drug administration and the like. The various data in the EMRs 23 have been input by use of the client terminal apparatus 12, and can be viewed from the client terminal apparatus 12.

The image server apparatus 22 is a PACS server (Picture Archiving and Communication System). An image database 22A or DB is combined with the image server apparatus 22, and stores diagnostic images 24. Examples of the diagnostic images 24 are those formed by the CT (Computed Tomography), MRI (Magnetic Resonance Imaging), X-ray imaging, ultrasonography, endoscopy and other medical imaging. The diagnostic images 24 are produced in a data file format of the DICOM (Digital Imaging and Communication in Medicine). The diagnostic images 24 can be viewed by use of the client terminal apparatus 12.

A case ID or patient ID (identification data) is associated with the EMRs 23 and the diagnostic images 24 as key information, in a form of signs or alphanumeric data for identifying each patient. The EMRs 23 and the diagnostic images 24 can be searched and read out from the EMR database 21A and the image database 22A by use of the case ID or key information as a query.

Note that the server cluster 13 can include a healthcare management server, a genetic test server and the like in addition to the EMR server apparatus 21 and the image server apparatus 22. The healthcare management server manages healthcare management information after measurement of blood pressure, body weight and the like of a patient at his or her home. The genetic test server manages genetic test information as a result of a genetic test of the patient. Recently, a simplified technique for the genetic test has been greatly developed, for example, a portable genetic test kit and test results can be dispatched to and from each patient. The genetic test will be used more widely in the future.

Figure 2:
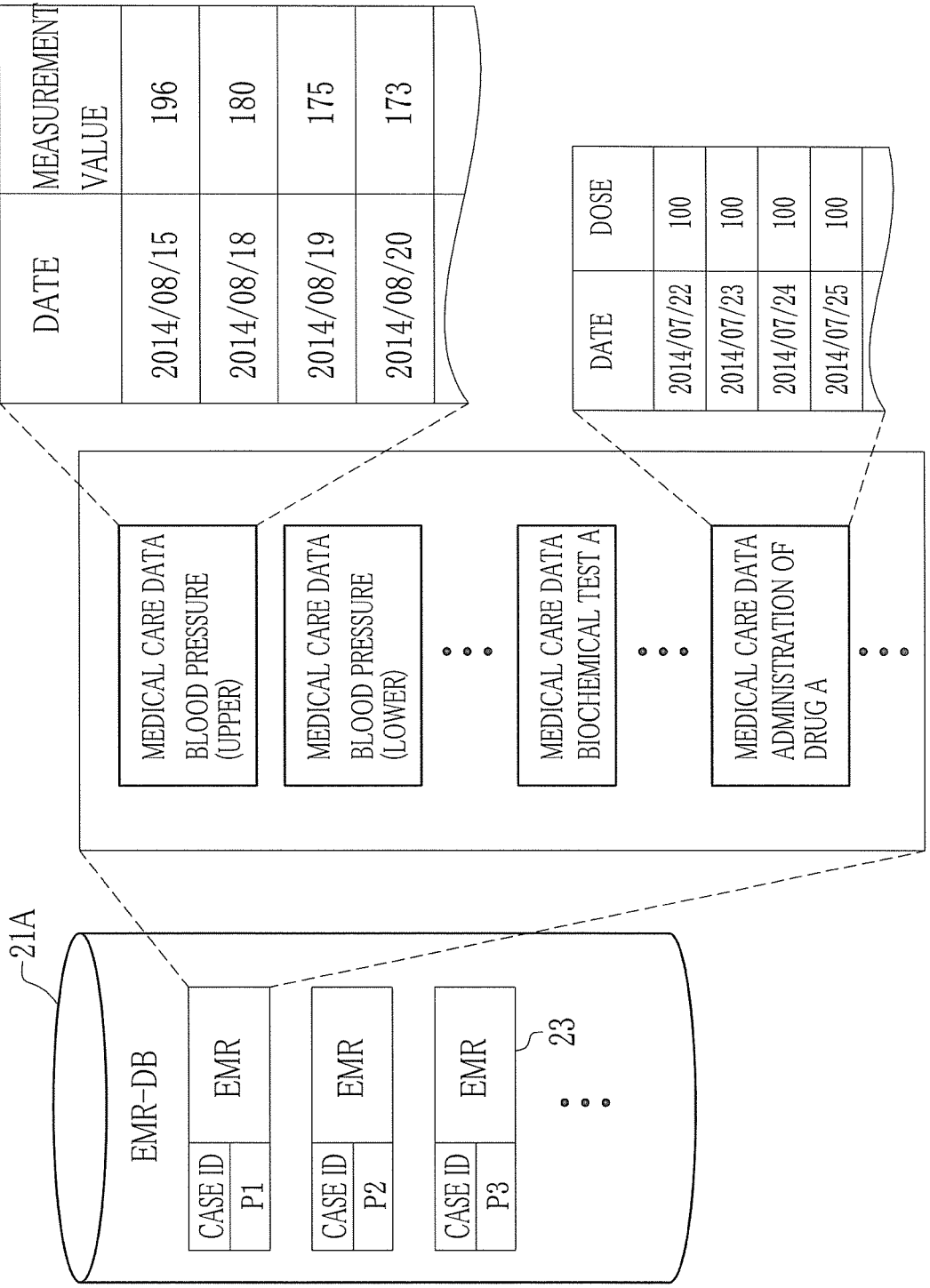
FIG. 2 is a data chart illustrating EMRs.

In FIG. 2, the EMRs 23 in the EMR database 21A are managed for respective patients by use of case IDs, such as P1, P2, P3 and so on. Information in the EMRs 23 includes the case ID, personal information (not shown) and medical care data. Examples of the personal information include a name, sex, birthday, age, address, telephone number and the like of the patient. The medical care data are recorded in a time sequential manner in the arrangement of list items, such as blood pressure (upper), blood pressure (lower), biochemical test A, administration of a drug A, and the like. The medical care data, in addition to those depicted in FIG. 2, include progress data, measurement values of vital signs, and treatment data. Examples of the progress data include results of questionnaire and check-up. Examples of the vital signs are a heart rate, respiratory rate and body temperature in addition to the blood pressure. Examples of the treatment data include intervention, surgery and the like. Assuming that the healthcare management server or genetic test server is used, the medical data to be added to the data in the EMRs 23 include healthcare management information from the healthcare management server or genetic test information from the genetic test server.

A record of one case of list items in the medical care data includes date/time information, such as a date/time of a patient visit, a date/time of a diagnostic test, a date/time of measurement, a date/time of drug administration (date/time of its use or date/time of the administration), and patient health information, such as content of questionnaire, a result of diagnosis, a test value, a measurement value, and dose of a drug. Assuming that the list item is the drug administration, an example of the drug administration at one time may be "dose of a particular amount per one day and continuation for five days", because effect of the drug administration may require a certain period. For this example, a date/time scheduled for the use of the drug is recorded as the date/time of the drug administration.

Figure 3:
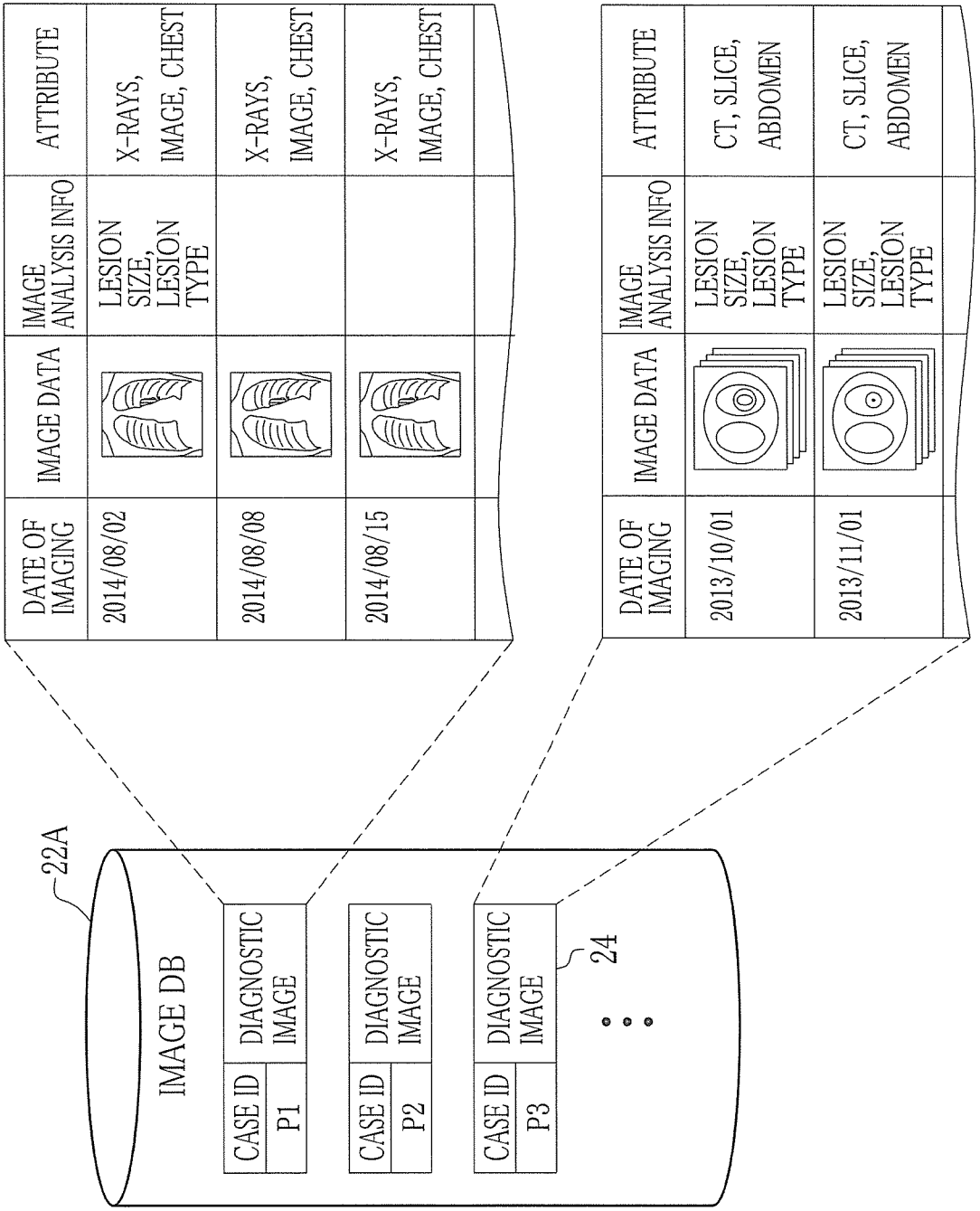
FIG. 3 is a data chart illustrating diagnostic images.

In FIG. 3, the diagnostic images 24 in the image database 22A are managed for each patient in association with the case ID in the same manner as the EMRs 23. Data of various attributes are associated with the diagnostic images 24 as associated information, including the case ID, calendar date of the imaging, image analysis information, modality, image type, body part and the like. Examples of the modalities are X-ray imaging and CT imaging. Examples of the image types are X-ray images and slices. Examples of the body parts are chest, abdomen and the like. The modality of the medical imaging is used as a list item of the medical care data. The image server apparatus 22 transmits the diagnostic images 24 to the diagnosis support server apparatus 11, the client terminal apparatus 12 and the like as medical care data together with the associated information such as image analysis information and attributes.

In the X-ray imaging, one image is created generally in one diagnostic process of the imaging. In the CT imaging, in contrast, a plurality of the diagnostic images 24 (slices) are created in one diagnostic process of imaging. For this case, a common test ID is allocated to the diagnostic images 24 (slices) to express that the diagnostic images 24 are derived from the single diagnostic process of imaging. The diagnostic images 24 are managed as one group. This is the same assuming that a plurality of X-ray images are created in one diagnostic process of the imaging.

The image analysis information is related to a size, type and the like of a lesion in the diagnostic images 24. Assuming that the medical imaging is ultrasound imaging, the image analysis information also includes a blood flow rate obtained by analyzing an ultrasonic image.

Each one of the diagnosis support server apparatus 11, the client terminal apparatus 12, and the EMR server apparatus 21 and the image server apparatus 22 in the server cluster 13 is constituted by a computer and programs installed therein. Examples of the computer are a personal computer, server computer, workstation and the like. The programs include control programs and application programs. The control programs are an Operating System (OS) and the like. The application programs are client programs, server programs and the like.

Figure 4:
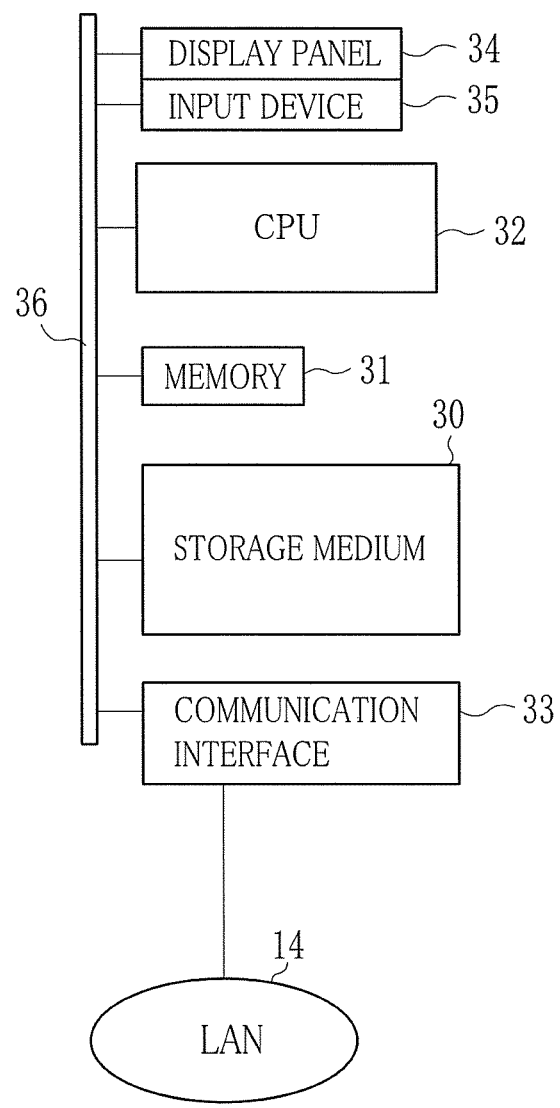
FIG. 4 is a block diagram schematically illustrating circuit devices in a computer for diagnosis support.

In FIG. 4, the computer constituting each of the diagnosis support server apparatus 11, the client terminal apparatus 12 and the like is basically equal, and includes a non-transitory storage medium 30 or storage device, a non-transitory memory 31, a CPU 32 (central processing unit), a communication interface 33, a display panel 34 and an input device 35. A data bus 36 interconnects those circuit devices.

The storage medium 30 is a hard disk drive incorporated in the computer constituting the diagnosis support server apparatus 11, the client terminal apparatus 12 or the like or connected to the computer by a cable, network or the like. Also, the storage medium 30 may be a disk array having plural hard disk drives. The storage medium 30 stores a control program and various application programs such as the Operating System (OS), and display page data for control pages associated with the programs.

The memory 31 is a working memory with which the CPU 32 performs tasks. The CPU 32 loads the memory 31 with the program read from the storage medium 30, and controls various circuit elements in the computer by performing the tasks according to the program.

The communication interface 33 is a network interface for transmission control of various data by use of the LAN 14. The display panel 34 displays the various control pages according to operation of the input device 35, such as a computer mouse, keyboard or the like. A function of input is provided in the control page according to the GUI (Graphical User Interface). The computer for the diagnosis support server apparatus 11, the client terminal apparatus 12 or the like receives inputs of command from the input device 35 by use of the control page. In the following description, a sign A will be added to each of reference signs of components in the computer constituting the diagnosis support server apparatus 11. A sign B will be added to each of reference signs of components in the computer constituting the client terminal apparatus 12.

Application programs (software) are installed in the client terminal apparatus 12, including an EMR program for viewing and editing the EMRs 23, an image viewing program for viewing the diagnostic images 24, and a viewer program for viewing the information page 15.

Figure 5:
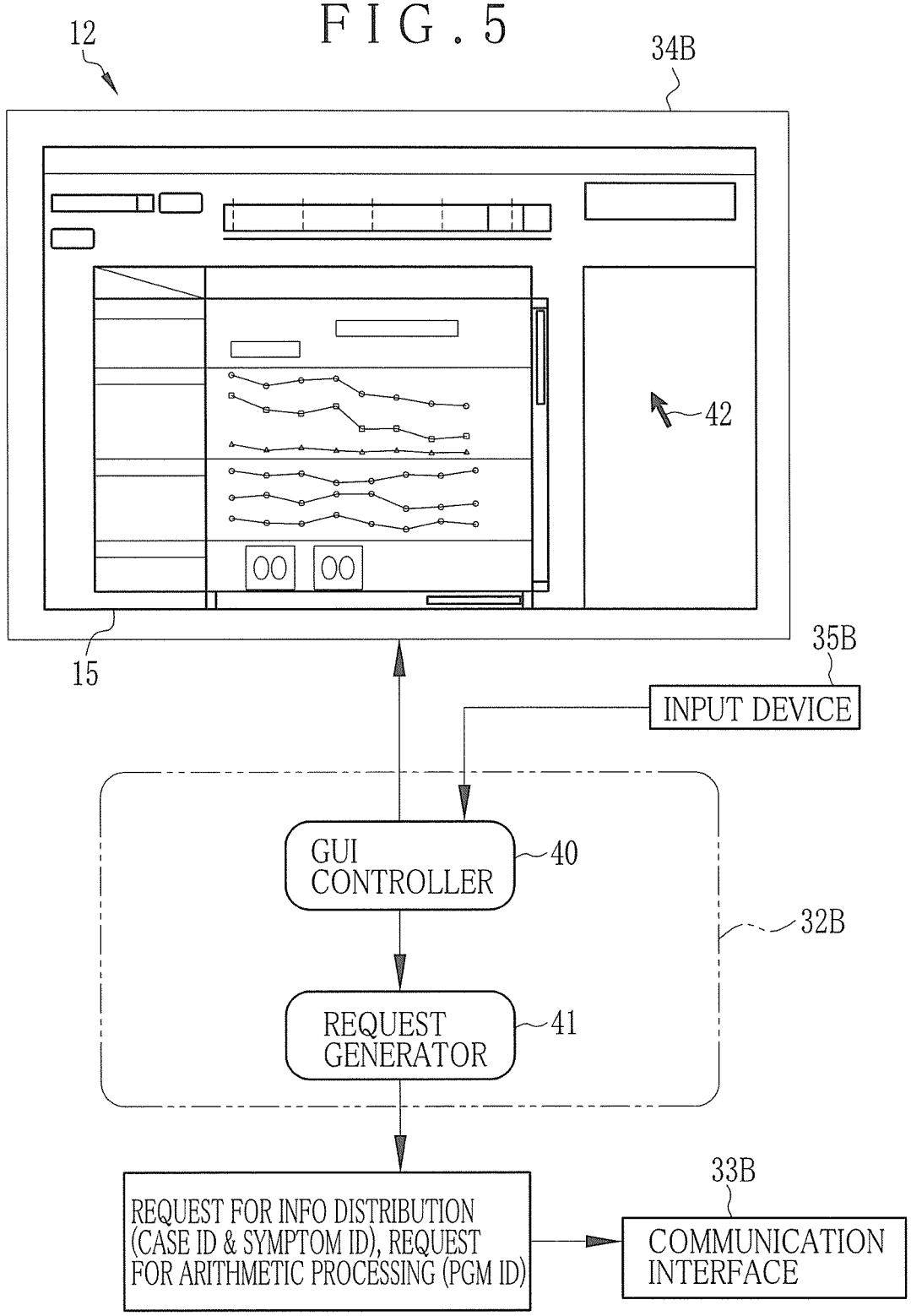
FIG. 5 is a block diagram schematically illustrating a client terminal apparatus.

In FIG. 5, a GUI controller 40 and a request generator 41 are established in a CPU 32B of the client terminal apparatus 12 in cooperation with a non-transitory memory 31B in case the viewer program for the information page 15 is run. A display panel 34B is driven by the GUI controller 40 with a web browser to display the information page 15 from the diagnosis support server apparatus 11. A cursor 42 is displayed on the information page 15 and operable with a button of a mouse and the like. An input device 35B is operated manually to input a command signal to control the information page 15 by use of the cursor 42.

The request generator 41 with a communication interface 33B transmits various requests toward the diagnosis support server apparatus 11 in response to command signals of the input device 35B by use of the GUI controller 40. The various requests include a request for the information distribution of the information page 15, a request for arithmetic processing and the like. A case ID is generated at the time of initially generating the information page 15. The request for the information distribution inclusive of the case ID is generated. Also, the request for the information distribution includes a request for updating or switching the information page 15. The request for the arithmetic processing is a command signal for running the diagnosis support programs 101 designated with the program ID, and processes outputting the diagnosis support information as a result of the arithmetic processing.

A symptom ID is code information allocated to each of symptoms, such as a lung cancer, stomach ulcer and the like. The program ID is code information allocated to each of the diagnosis support programs 101.

Figure 6:
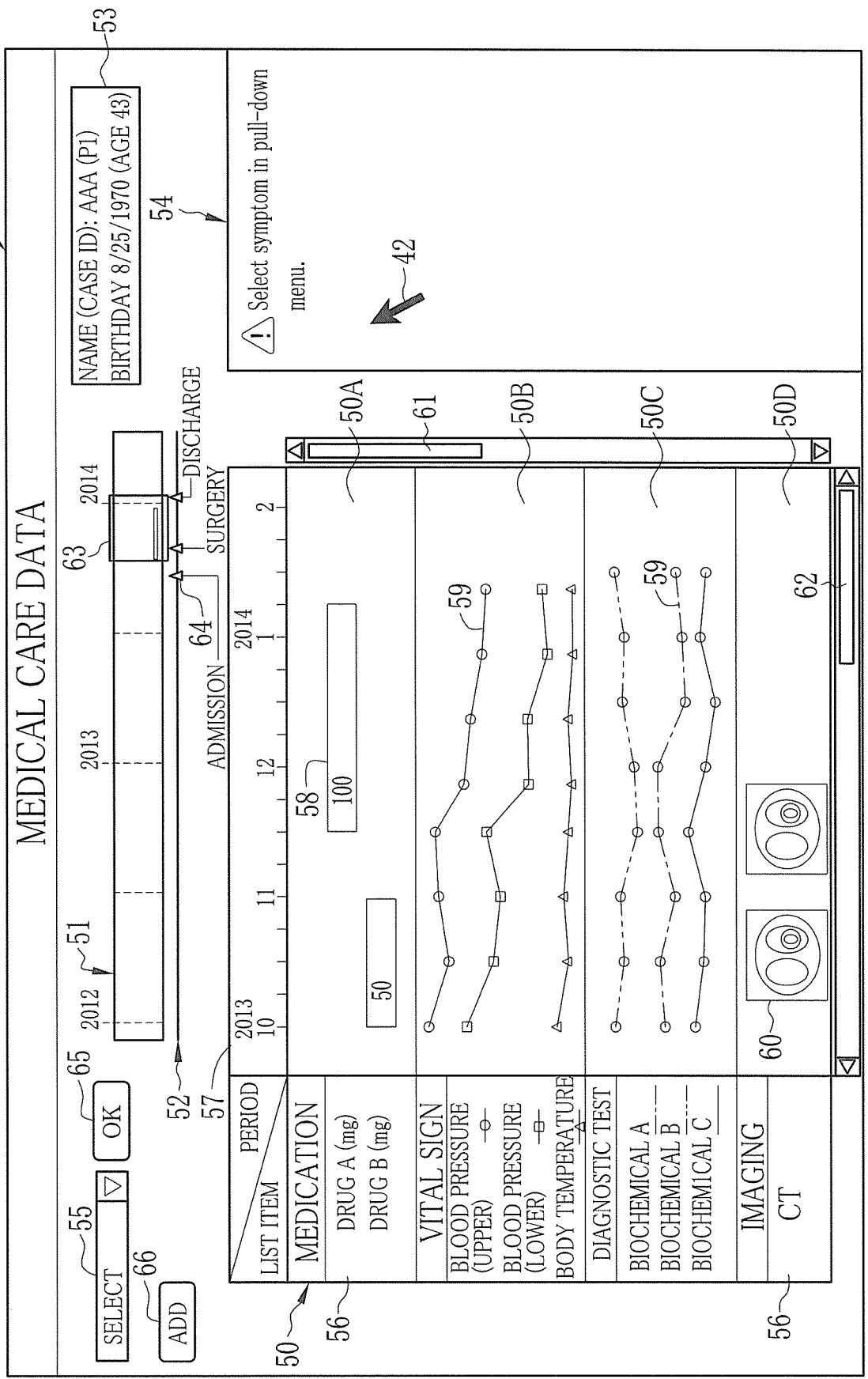
FIG. 6 is a screen view illustrating an information page.

In FIG. 6, the information page 15 has a record list 50 or medical care data display area, a time sequence area 51 or timeline bar area, a procedure area 52 for events in the workflow, a patient area 53, a message area 54 for information, and a pull-down menu 55.

A list item field 56 or data item field (item display area) and a time sequence field 57 or timeline bar field are disposed along its peripheral edges of the left and the upside. A vertical axis of the record list 50 extends for arrangement of medical care data. A horizontal axis of the record list 50 extends for a flow of time. The list item field 56 contains names of groups of list items of medical care data, such as medication, vital sign, diagnostic test and medical imaging, and names of list items, such as drugs A and B, blood pressure (upper and lower), body temperature, biochemical tests A, B and C, and CT imaging. The time sequence field 57 contains a first period of acquiring medical care data displayed in the record list 50 among all the medical care data in the entire time sequence of the medical care of the patient. A time scale of the year, month and day is disposed in the time sequence field 57. In FIG. 6, the first period is approximately three months and a half from October of 2013 until January of 2014.

Plural subsidiary areas are defined in the record list 50 and arranged in the vertical direction as indicated in the list item field 56, including a medication area 50A, a vital sign area 50B, a test area 50C and an imaging area 50D. The list item of the drug administration is allocated to the medication area 50A. The list item of the vital signs is allocated to the vital sign area 50B. The list item of the diagnostic tests is allocated to the test area 50C. The list item of the medical imaging is allocated to the imaging area 50D. A time period bar 58 is indicated in the medication area 50A to express calendar dates of starting and completing the drug administration in the first period, and a dose of the drug. In the list item field 56, the parentheses for the drug administration are indicated for the unit of the dose indicated at the time period bar 58.

Line graphs 59 or line charts are displayed in the areas 50B and 50C and formed by plotting test values of the vital signs and measurement values of the diagnostic tests in the first period. Block cells in the list item field 56 for the vital signs and diagnostic test indicate guide information of the line graphs 59. A thumbnail image 60 of the diagnostic images 24 obtained in the first period is displayed in the imaging area 50D. The time period bar 58, plotting of the measurement values and test values for the line graphs 59, and the thumbnail image 60 are disposed in compliance with dates of the drug administration, measurement and tests.

Scroll bars 61 and 62 are displayed and operable for scrolling the record list 50 vertically and horizontally. In case the scroll bar 61 is scrolled, an active display area of the list item field 56 and the subsidiary areas can be changed vertically. In case the scroll bar 62 is scrolled, a display size of the first period can be changed horizontally.

The time sequence area 51 is an area for displaying a second period, which is relatively longer than the first period in the time sequence field 57. A date range 63 is additionally disposed with the time sequence area 51, where indication of years is provided. The date range 63 indicates correspondence of the first period to a portion of the second period. The date range 63 corresponds to the size of the first period within the range of the second period. In FIG. 6, the first period is approximately three months and a half. The date range 63 corresponds to the size of approximately three months and a half in the scale of the second period.

The date range 63 is movable horizontally relative to the time sequence area 51 in response to an input action to the scroll bar 62. Also, a display size of the first period of the date range 63 can be changed by moving the date range 63 horizontally or changing the horizontal size of the date range 63. Note that the first period can be before acquiring the newest medical care data by a predetermined length of time, or can be designated manually by a doctor at the same time as inputting the case ID in the start page.

The procedure area 52 displays a date and time of medical events in the medical care of the patient, together with an event name and an arrow 64 for the time sequence area 51. Examples of the medical events include hospital admission, surgery and hospital discharge. The patient area 53 displays basic information of the patient of the case ID input in the start page of the view application, such as a name, case ID, birthday and the like of the patient.

The message area 54 displays various data for notification to a doctor. In FIG. 6, a message for encouraging selection of a symptom with the pull-down menu 55 is displayed in the message area 54.

The pull-down menu 55 is used for selecting a symptom. All of the symptoms are displayed in the pull-down menu 55, such as symptoms A, B and the like in FIG. 8. An OK button 65 is disposed beside the pull-down menu 55. An add button 66 is disposed under the pull-down menu 55. Pressing or clicking the add button 66 with the cursor 42 can add the pull-down menu 55 newly. It is possible to select a complex disease, such as a complex disease A-B in FIG. 8. In general, complex diseases are observed largely in elderly persons. The number of patients suffering a complex disease has been increased recently due to the problem of the rapidly aging society, so that the function suitable for the complex diseases in the present invention is particularly useful.

In case the pull-down menu 55 is operated by use of the cursor 42, a symptom is selected. In case the OK button 65 is clicked or pressed, a request for information distribution of a symptom ID of the selected symptom is transmitted by the client terminal apparatus 12 to the diagnosis support server apparatus 11. The diagnosis support server apparatus 11 distributes the information page 15 with updated information. Also, a search bar can be displayed for search candidates of predicted diseases according to a symptom of a patient by use of the symptom as a search query.

Figure 7:
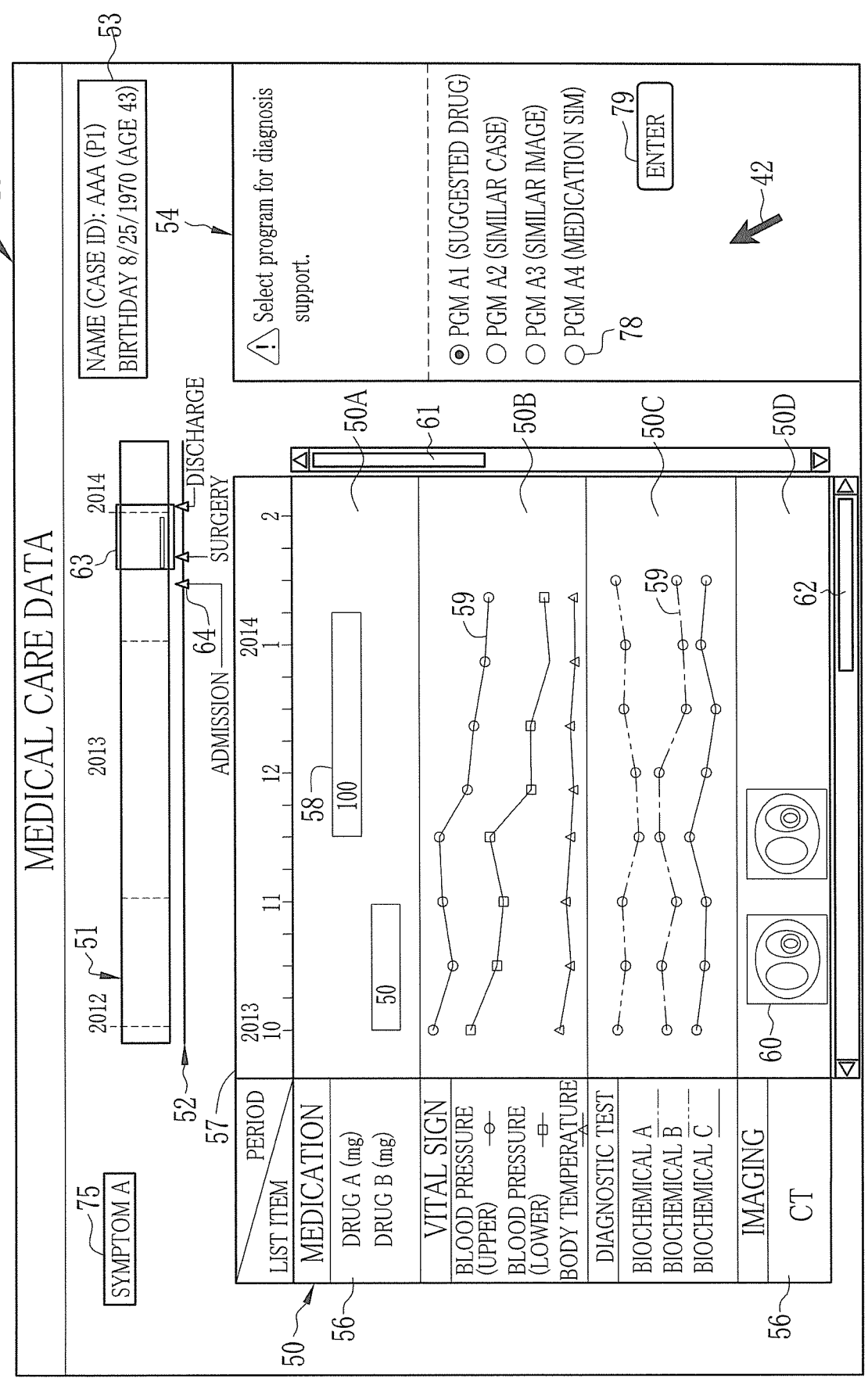
FIG. 7 is a screen view illustrating the information page for selection of diagnosis support programs.

Selecting the symptom updates the content of the information page 15 as illustrated in FIG. 7. For example, the symptom A is selected in the pull-down menu 55.

A mapping table 80 of symptoms in FIG. 8 is used for updating the information page according to the symptom selection. The mapping table 80 indicates relationships between the symptoms (symptoms A, B and the like), display list items of medical care data for display in the information page 15, and the diagnosis support programs 101. For example, display list items of drugs A and B, blood pressures (upper and lower), biochemical tests A, B and the like, and CT imaging are registered for the symptom A. Registered examples of the diagnosis support programs 101 are programs A1, A2, A3, A4 and the like.

According to the mapping table 80, list items registered for the respective selected symptoms are displayed in the information page 15. The number of the list items with displayable medical care data depends upon a display size of the page, so that the number of the displayable list items without scrolling the page is limited. Also, it is likely that unnecessary list items or list items of relatively low importance are included according to the types of the symptoms. Visual perceptibility of the information page 15 can be made higher by limiting the displayed list items to the list items with high importance. This being so, the displayed list items in the information page 15 are registered for the respective symptoms.

Assuming that the list items of the initial setting are different from the list items registered for the selected symptom, the list items are changed according to the selected symptom. However, there is no change in the list items assuming that the list items of the initial setting are the same. In the embodiment, the list items of the initial setting are the same as the list items of the symptom A. No change occurs in the list items in the example of the information page 15 in FIGS. 6 and 7.

Functions in the diagnosis support programs 101 are differently used for various symptoms in view of suitability for the purpose. Thus, a plurality of the diagnosis support programs 101 are prepared for the various symptoms and registered in the mapping table 80. The following is the functions of the programs A1-A4 registered for the symptom A.

The program A1 performs a function of detecting a drug in consideration of a symptom of a patient, and informing the suggested drug as diagnosis support information. The program A2 performs a function of searching a similar patient case similar to the patient case of the patient's symptom according to the test values and vital signs of the patient, and informing the similar patient case as diagnosis support information. The program A3 performs a function of searching a similar image similar to the diagnostic image of the patient, and informing the similar diagnostic image as diagnosis support information. The program A4 performs a function of predicting changes in the test values and vital signs according to a type, dose and administration of the drug, and providing simulation information of a result of the predicted changes as diagnosis support information.

For the symptom B, list items of drugs A and C, blood pressure (upper and lower), biochemical tests E, B and the like and CT imaging are registered as displayed list items. Plural programs B1, B2, B3, B4 and so on are registered for the diagnosis support programs 101. For a complex disease A-B of the symptoms A and B, list items of drugs A, B and C, blood pressure (upper and lower), biochemical tests A, B, E, F and G, CT imaging and ultrasonic imaging are registered as displayed list items. Plural programs AB1, AB2, AB3, AB4 and so on are registered for the diagnosis support programs 101. The functions of the programs B1-B4 and the programs AB1-AB4 are similar to those of the programs A1-A4.

A non-transitory storage medium 30A or storage device in the diagnosis support server apparatus 11 stores the mapping table 80. See FIG. 11. The diagnosis support programs 101 for the mapping table 80 are previously registered by management personnel of the diagnosis support server apparatus 11 or a doctor using the client terminal apparatus 12. The diagnosis support programs 101 in the mapping table 80 can be updated at any time of requirement.

In FIG. 7, a symptom area 75 is formed in the information page 15 in place of the pull-down menu 55, the OK button 65 and the add button 66 in FIG. 6. A symptom name of the selected symptom in the pull-down menu 55 is indicated in the symptom area 75, such as symptom A.

Also, a message to a user is displayed in the message area 54 for selection of the diagnosis support programs 101 for use. In addition, the name and function of the diagnosis support programs 101 set in the mapping table 80 are displayed in a list form, such as the program A1 for the drug suggestion. A radio button 78 and an enter button 79 are displayed for selecting one of the diagnosis support programs 101 displayed in the list form. In case the enter button 79 is pressed or clicked after selecting the diagnosis support program 101, the diagnosis support program 101 is run in the diagnosis support server apparatus 11.

Figure 9:
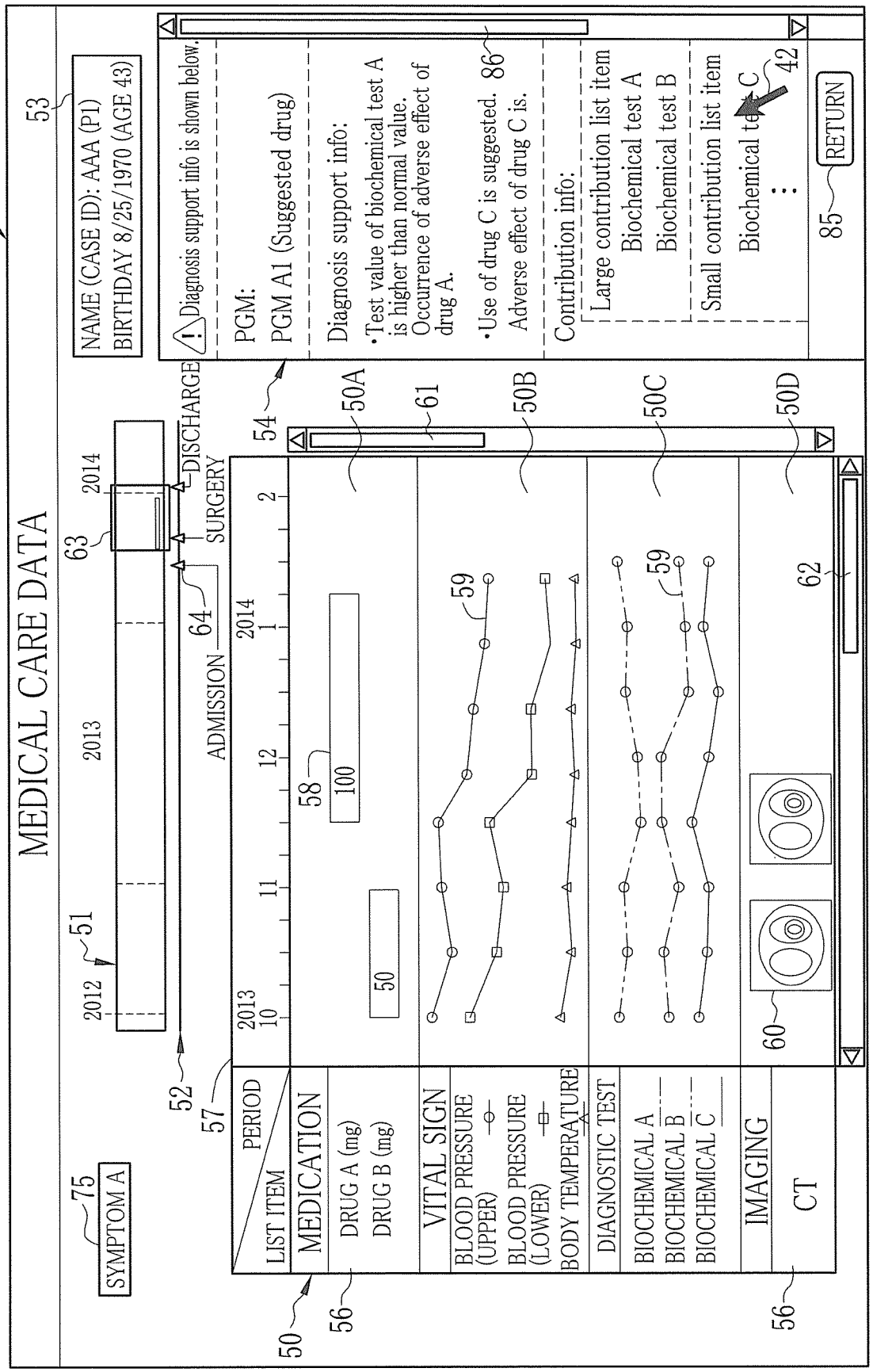
FIG. 9 is a screen view illustrating an information page with diagnosis support information.

In FIG. 9, the diagnosis support information is displayed in the message area 54 of the information page 15. The message area 54 displays a guide message for the diagnosis support information, a program name of the diagnosis support programs 101 for use, diagnosis support information, contribution information, and a return button 85 for return to the state of FIG. 7. An example of the guide message is "Diagnosis support info is shown below". An example of the program name is "PGM A1 (Suggested Drug)". Also, a scroll bar 86 is displayed in the message area 54 in the case of a large data amount of display data. The message area 54 can be scrolled vertically by operation of the scroll bar 86.

In FIG. 9, the program A1 for the suggested drug administration is selected. Then a message or comment for suggesting the use of a drug C is displayed as diagnosis support information in a different manner from the drugs A and B used presently. Also, the diagnosis support information includes description of observation of the test value of the biochemical test A and notice of adverse effect of the drug C.

The diagnosis support program 101 determines diagnosis support information by running with input list items or plural list items of the medical care data of a patient. The contribution information is information related to a large contribution list item, of which a contribution value (relevancy score) relative to diagnosis support information is equal to or higher than a predetermined threshold among plural input list items of the medical care data input to the diagnosis support program 101. Relevancy to the result of the arithmetic processing is high according to highness in the contribution value of the list item. Displaying the large contribution list item facilitates understanding of a process (logic flow) of determination, for example, relevancy of input list items in the process of determination in the diagnosis support programs 101.

For the program A1, plural list items of the biochemical tests A, B, C and the like in the medical care data are input to determine and output diagnosis support information. In the contribution information of the embodiment, the biochemical tests A and B are large contribution list items among the input list items. It is found that contribution of medical care data of the biochemical tests A and B is high in determining the present diagnosis support information with the program A1, so that part of the process (logic flow) of determination in the program A1 can be clarified. The doctor can utilize the diagnosis support information with reliability, as he or she can visually check acceptability of the process of the determination, because of higher system visibility. Furthermore, let the doctor judge that a biochemical test E (not shown) is important. He or she can find that the biochemical test E is not included in the large contribution list items. It is possible for the doctor not to utilize the result of the determination of the program as diagnosis support information with his or her decision.

In case there are plural large contribution list items, the large contribution list items are arranged in the information page 15 in a display sequence of highness of the contribution value. In the embodiment, the contribution value of the biochemical test A is higher than that of the biochemical test B, so that those are arranged in the display sequence of A and then B. It is easy to observe the list items as one with the higher contribution value is disposed in a high location in the information page 15. Checking the list items can be efficient because the list items are read in the sequence of highness of the contribution value.

Also, the contribution information includes not only the large contribution list item but also a small contribution list item of which a contribution value (relevancy score) in relation to the diagnosis support information as a result of the determination is (equal to or) smaller than a predetermined threshold. The small contribution list item is a list item used in the determination for the diagnosis in the same manner as the large contribution list item, but has a relatively lower contribution value than the large contribution list item. The information page 15 displays the large contribution list item and the small contribution list item in a distinct form. The small relevancy to the process (logic flow) of determination in the diagnosis support programs 101 is visually clarified in the information page 15 by addition of the small contribution list item to the large contribution list item in the contribution information. Thus, the content of the process of the determination can be informed more clearly with the system visibility than indication of only the large contribution list item. Specifically, small contribution of the biochemical test C can be clarified in the use of the program A1 in the embodiment.

Figure 10:
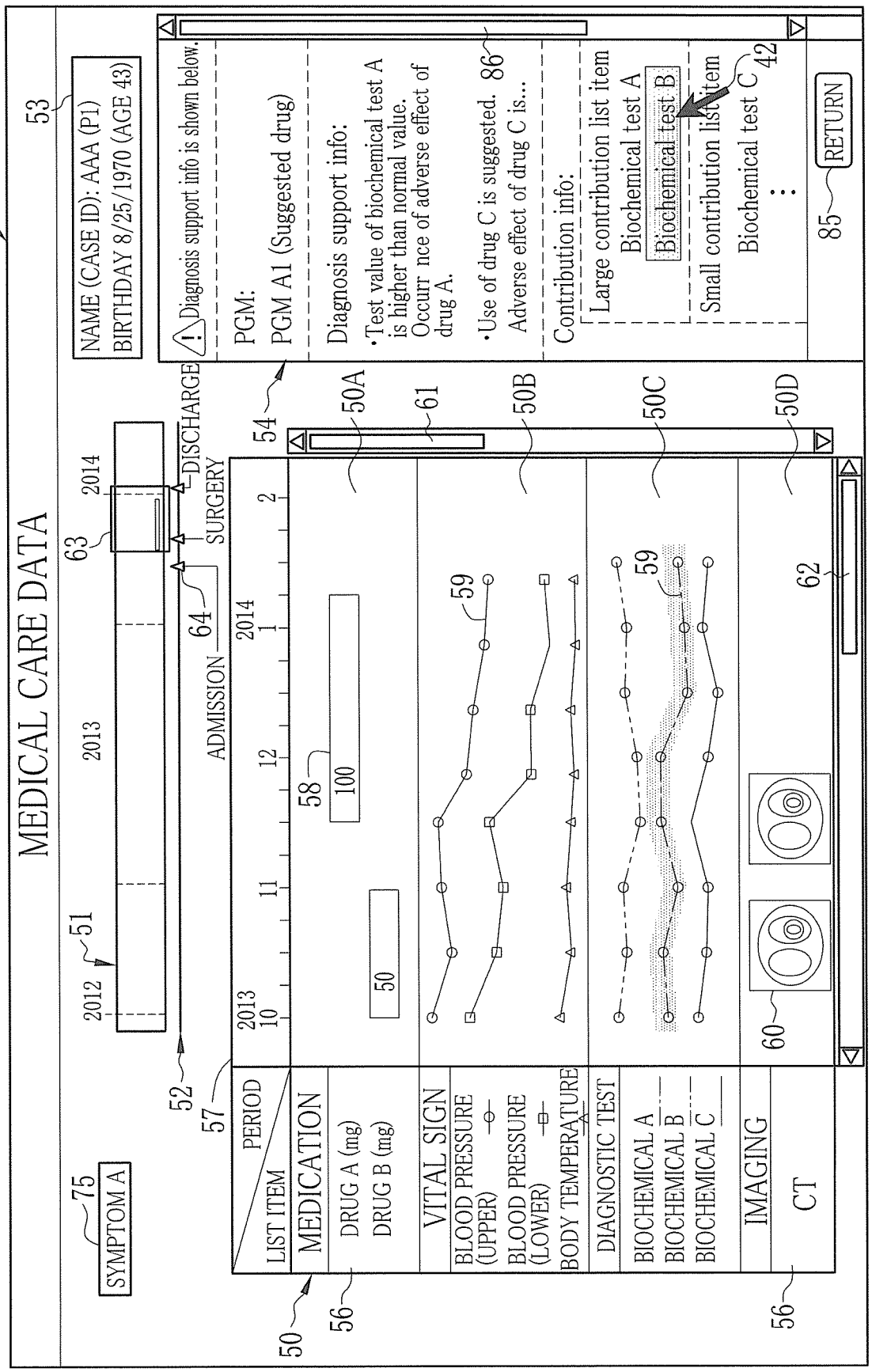
FIG. 10 is a screen view illustrating designated large contribution list items with an emphasis.

In FIG. 10, assuming that one of the large contribution list items included in the contribution information is specified in the information page 15, medical care data corresponding to the specified large contribution list item is displayed visibly. Let the biochemical test B be specified by use of the cursor 42 as one large contribution list item in FIG. 10. One of the line graphs 59 corresponding to the biochemical test B is indicated with the emphasis as hatched in the test area 50C in response to the designating operation. Examples of the emphasis include a highlighted form, large thickness or variable thickness of lines of the line graphs, and the like.

Consequently, medical care data corresponding to the specified large contribution list item can be found in the record list 50, and can be referred to for the proper purpose. Furthermore, an additional window area can be used to display time sequential data of numerical values as a basis of the line graphs 59, together with the emphasis for the line graphs 59. It is possible to check the numerical values easily.

Various pointing device gestures (mouse gestures) of the computer mouse can be used for pointing of the cursor 42, including clicking and mouseover. In the clicking, the cursor 42 is positioned at an object of interest in the display, then a mouse button of the mouse is depressed. In the mouseover, the cursor 42 is only positioned at the object of interest to perform the designation without depressing a mouse button.

Also, it is possible serially to display list items with emphasis according to highness of the contribution value automatically without use of the cursor 42 for designation. This is effective in simplifying check of the list items without manual action. Also, this structure is useful in the case of scroll, which is required for partial display of numerous list items among those which are not displayed at one time.

It is possible that assuming that no medical care data is displayed in the record list 50, link information (namely, data address of a location) of the medical care data can be displayed and referred to for acquiring medical care data corresponding to the large contribution list items in response to designating the large contribution list items. Also, the record list 50 can be scrolled to display medical care data of interest in the record list 50. Furthermore, it is preferable to display and refer to medical care data in relation to the small contribution list items in response to designating the small contribution list items.

The display processing of the information page 15 can be performed by execution of a script or program component embedded in the data of the XML format of the information page 15, or by modifying the information page 15 in the diagnosis support server apparatus 11 according to a request from the client terminal apparatus 12 to transmit the information page 15 of the modified form.

In FIG. 11, a control program 100 and a plurality of the diagnosis support programs 101 are stored in the storage medium 30A of the diagnosis support server apparatus 11 as application programs. The control program 100 is run in the diagnosis support server apparatus 11 for performance of the computer as a diagnosis support apparatus. Also, the mapping table 80 in FIG. 8 is stored in the storage medium 30A.

In a CPU 32A (central processing unit) of the diagnosis support server apparatus 11, a request processor 110, a data readout unit 111, a program controller 112, a page generator 113, a display processor 114 for pages, and an information acquisition unit 115 are established by running the control program 100 in cooperation with the memory 31.

The request processor 110 (request receiving unit) performs a function of receiving requests from the client terminal apparatus 12, such as a request for the information distribution and a request for the arithmetic processing. Specifically, the request processor 110 receives the request for the information distribution with a designated case ID and symptom ID. Also, the request processor 110 receives the request for the arithmetic processing with a designated program ID. The request processor 110 instructs the data readout unit 111 to operate for the information distribution with the designated case ID and symptom ID, and instructs the program controller 112 (diagnosis support device and evaluator) to operate for the arithmetic processing with the designated program ID.

The data readout unit 111 (data acquisition unit) accesses the EMR database 21A and the image database 22A and reads out medical care data according to requirements.

The data readout unit 111 upon receiving the case ID from the request processor 110 accesses the EMR database 21A and the image database 22A, and reads out medical care data of an initially predetermined list item among the medical care data of the input case ID. Also, the data readout unit 111 upon receiving the symptom ID refers to other displayed list items for respective symptom IDs registered in the mapping table 80, and reads out medical care data of the displayed list items. The data readout unit 111 reads out plural program IDs of the diagnosis support programs 101 for respective symptoms registered in the mapping table 80 in order to display a list of the diagnosis support programs 101 on the information page 15. See FIG. 7. The medical care data and program ID being read out are transmitted to the page generator 113.

Figure 12:
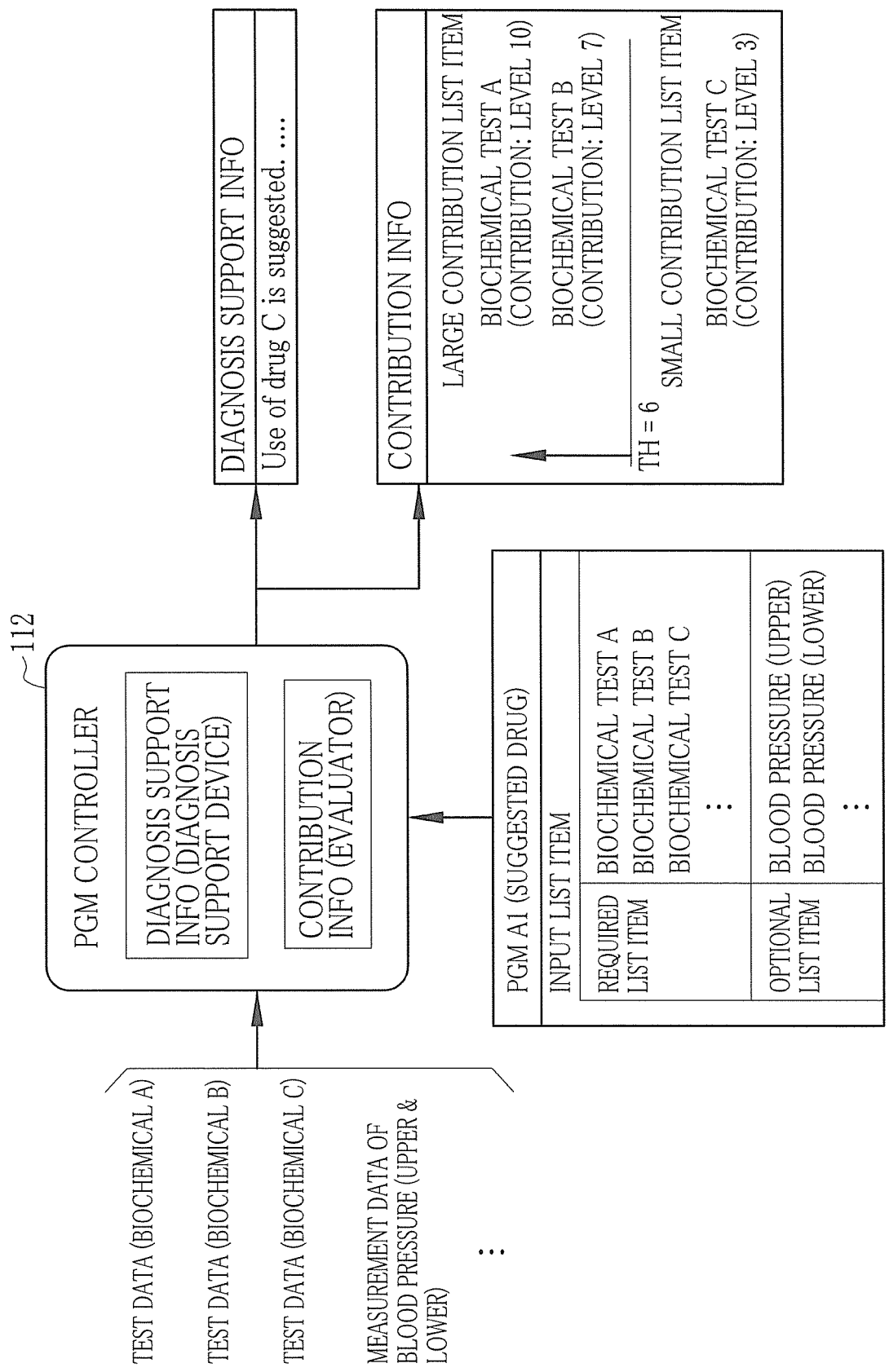
FIG. 12 is a data chart illustrating a diagnosis support program for suggesting a drug.

In FIG. 12, the program controller 112 reads out the diagnosis support program 101 being designated, and performs the arithmetic processing according to the diagnosis support program 101, to perform a task of obtaining the diagnosis support information and a task of obtaining the contribution information.

The program controller 112 transmits information of the input list items set for each of the diagnosis support programs 101 to the data readout unit 111, and designates the list items of the medical care data to be acquired. Examples of the input list items in relation to the program A1 of the embodiment include required list items required for the arithmetic processing and optional list items of which use is optional for the arithmetic processing. The optional list items do not need being input, or do not need being used after input. It is possible to use or not to use the optional list items according to a condition of other input list items. A setting of input list items is predetermined according to specifics of the diagnosis support programs 101.

In the program A1, biochemical tests A, B, C and the like are set as required list items. Blood pressures (upper and lower) and the like are set as optional list items. Medical care data of those input list items read out by the data readout unit 111 are input to the program controller 112 as parameters for arithmetic processing.

The program controller 112 designates input list items for the data readout unit 111, which reads out medical care data from the EMR database 21A and the image database 22A in association with the specified input list items. The medical care data is input by the data readout unit 111 to the program controller 112 in association with the specified input list items.

The program controller 112 runs the diagnosis support program 101 according to the input medical care data, and determines the diagnosis support information. As the program A1 has a function of obtaining a suggested drug, suggested drug information is determined as the diagnosis support information.

The contribution information is information related to a list item with contribution to determining the diagnosis support information among the list items of plural sets of diagnosis support information. In the embodiment, the contribution information includes a large contribution list item of which a contribution value is equal to or higher than a threshold, and a small contribution list item of which a contribution value is lower than the threshold. See FIG. 9.

The large contribution list item in FIG. 12 is set in comparison with the threshold TH, which is a level 6 according to 10 levels of the scale. The biochemical tests A and B with the levels 10 and 7 for the contribution value are the large contribution list items. The biochemical test C with the level 3 for the contribution value is the small contribution list item.

Figure 13:
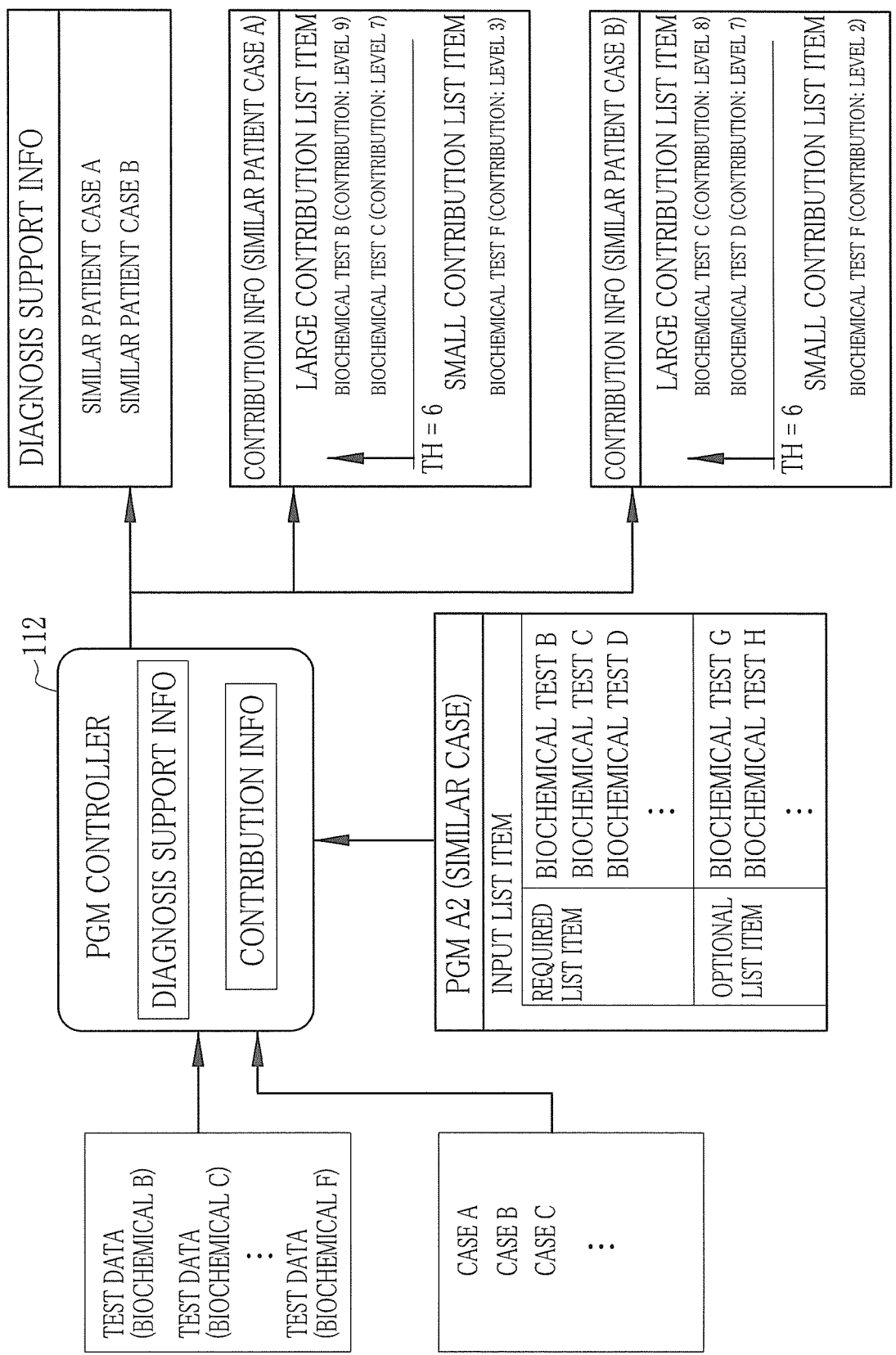
FIG. 13 is a data chart illustrating a diagnosis support program for searching a similar patient case.

In FIG. 13, selection of the program A2 as the diagnosis support program 101 is illustrated. The program A2 has a function of searching similar patient cases. The program controller 112 runs the program A2 to determine similar patient cases as diagnosis support information. In the program A2, required list items in the input list items are biochemical tests B, C, D and the like. In the similar patient case search, patient cases with similarity in changes of the time sequential data of the test values of those list items are acquired as similar patient cases. The patient cases are stored in a case database (not shown). A server combined with the database is included in the server cluster 13.

The program A2 is run in the program controller 112 to determine a similarity score by comparison between the medical care data of the biochemical tests B, C, D and the like of the patient read out by the data readout unit 111 and the cases acquired from the case database by the program controller 112. One of the cases with a relatively high similarity score being determined is judged as a similar patient case. As the plural input list items exist inclusive of the biochemical tests B, C and D in the embodiment, a similarity score is determined for each of the list items. For example, the similarity score of the time sequential data of the biochemical test B, that of the biochemical test C, and that of the biochemical test D are determined.

The program A2 run by the program controller 112 evaluates the similarity score between list items entirely, to obtain similar patient cases selectively. In obtaining the contribution information in relation to obtaining the similar patient cases, the contribution value is acquired according to the similarity score between the list items with the highest relevancy to the entire evaluation. For example, the contribution value is judged as a high value according to highness of the similarity score between respective list items. In the similar patient case A in the embodiment, the similarity score to the medical care data of the patient is high in relation to the list items of the biochemical tests B and C, which are judged as large contribution list items with high contribution values. Also, the similarity score to the medical care data of the patient is low in relation to the list item of the biochemical test F, which is judged as a small contribution list item with a lower contribution value than the threshold TH.

In the similar patient case B, a similarity score is high in relation to the biochemical tests C and D, which are large contribution list items. However, a similarity score is low in relation to the biochemical test F, which is a small contribution list item because its contribution value is lower than the threshold TH. In the similar patient case search, plural similar patient cases may be detected, and it is likely that plural sets of the diagnosis support information are generated. Note that it is possible to extract similar patient cases in the program A2, and to determine the contribution information in the client terminal apparatus 12 or a discrete terminal apparatus other than the diagnosis support server apparatus 11. For this structure, the diagnosis support server apparatus 11 transfers information of the similarity score to the client terminal apparatus 12 together with the acquired similar patient cases.

Assuming that there are plural sets of the diagnosis support information with the similar patient cases A and B or the like as illustrated in FIG. 14, it is preferable to change over display of the contribution information including the large contribution list items in the message area 54 by operating the cursor 42. On a left side in FIG. 14, the similar patient case A is designated by the cursor 42. Contribution information of the similar patient case A is displayed. On the right side in FIG. 14, the similar patient case B is designated by the cursor 42. Contribution information of the similar patient case B becomes displayed upon the changeover. In short, contribution information including a large contribution list item is displayed in response to designation of the contribution information. This structure is advantageous for facilitating the comparison between the plural sets of the contribution information in view of utilization.

Also, the record list 50 in the information page 15 can be changed over in response to designating the diagnosis support information. In the embodiment, only the biochemical tests B and C are displayed in the test area 50C as large contribution list items of the similar patient case A upon designating the similar patient case A with the cursor 42. In contrast, only the biochemical tests C and D are displayed as large contribution list items of the similar patient case B upon designating the similar patient case B. In the embodiment, only medical care data of the large contribution list items are displayed. However, it is possible to display medical care data with an emphasis as illustrated in FIG. 10 in correspondence with the large contribution list items of the designated diagnosis support information (similar patient cases) while medical care data of other list items remain displayed.

Figure 15:
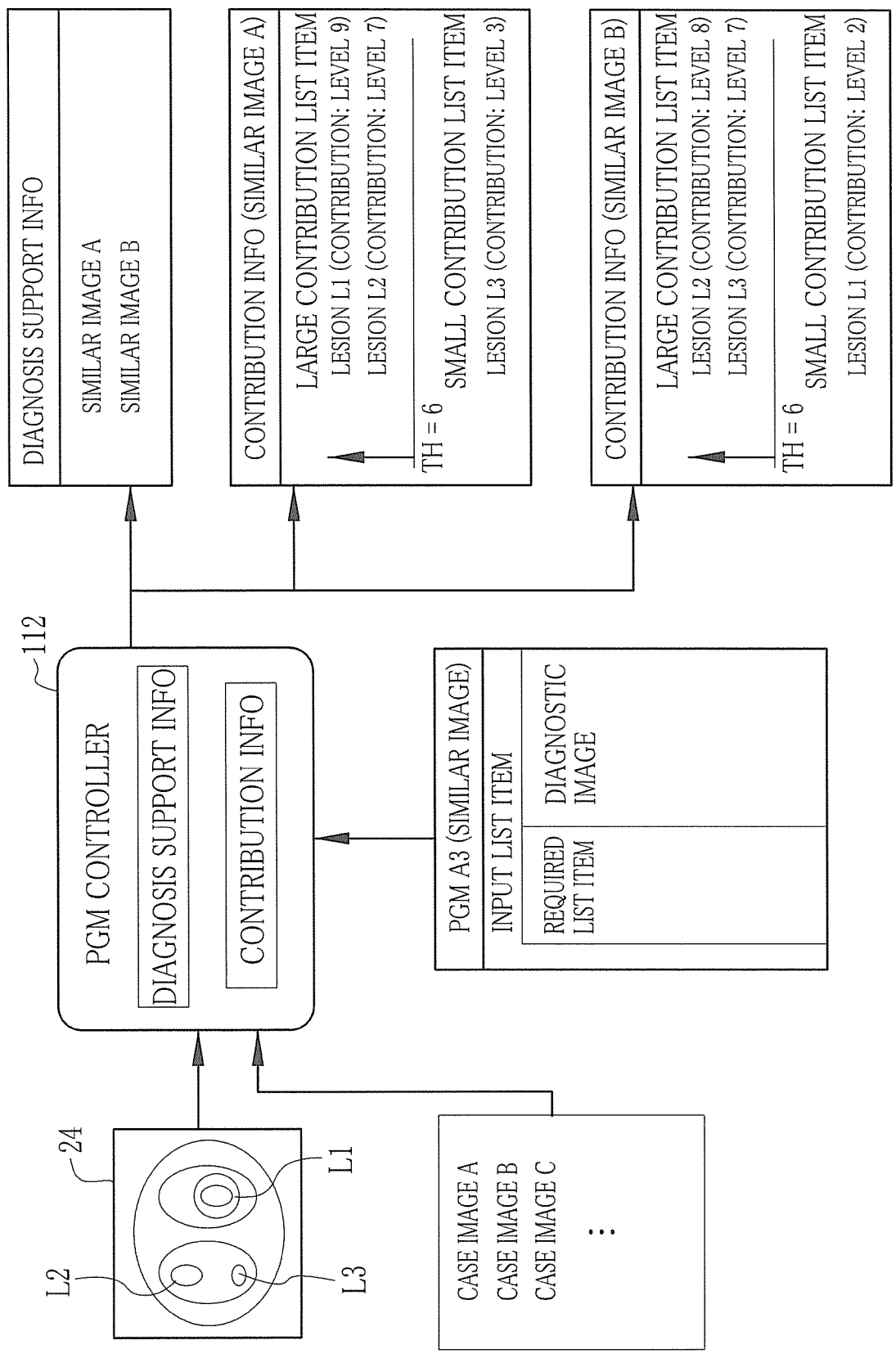
FIG. 15 is a data chart illustrating a diagnosis support program for similar image search.

In FIG. 15, selection of the program A3 as the diagnosis support program 101 is illustrated. The program A3 has a function of searching similar images. The program controller 112 runs the program A3 to determine similar images as diagnosis support information. In the program A3, a required list item in the input list items is diagnostic images of a patient. There is no optional list item. In the similar image search, symptom images with similarity in a form of a lesion in the diagnostic images are acquired as similar images. Thus, the images of the lesion acquired from the diagnostic images are plural input list items.

Assuming that diagnostic images are CT images, then the input list items are lesions extracted from plural slice images (diagnostic images). Also, assuming that plural lesions L1, L2 and L3 are included in one of the diagnostic images 24, then the input list items are the lesions L1-L3.

The program A3 searches and reads out a case image from the case database as a similar image according to similarity of a lesion of the patient, in the same manner as the search of the program A2. At first, the program A3 in the program controller 112 determines a similarity score with the case image in relation to the plural lesions L1-L3. The similarity score in relation to the lesions L1-L3 is evaluated together, so that a combined similarity score is obtained. One of the case images of which the combined similarity score is typically high is judged as a similar image.

The contribution value is evaluated according to the similarity score of the plural lesions L1-L3. For example, let the similarity score of the lesion L1 be the highest among the lesions L1-L3 in relation to the designated similar image A. A rank order of highness of the contribution value is the lesion L1 and then the lesions L2 and L3. The lesions L1 and L2 are large contribution list items. The lesion L3 is a small contribution list item. In relation to the similar image B, a rank order of highness of the similarity score is the lesion L2 and then the lesions L3 and L1. Thus, the lesions L2 and L3 are large contribution list items.

In the similar image search, the display is changed over in the information page 15 in the same manner as FIG. 14 in a manner similar to the similar patient case search. In the similar image search, the thumbnail image 60 of the diagnostic image 24 displayed in the imaging area 50D of the record list 50 is displayed with an emphasis for a lesion as a large contribution list item related to the designated similar image upon designating one of plural similar images. For example, let the similar image A be designated. The lesions L1 and L2 as large contribution list items are displayed with an emphasis in the thumbnail image 60. Also, it is possible to obtain a similar image by use of the program A3 as the diagnosis support program 101 and to obtain the contribution information in the client terminal apparatus 12 or other devices, in the same manner as the similar patient case search.

In FIG. 11, the information acquisition unit 115 acquires the diagnosis support information and contribution information from the program controller 112. The information acquisition unit 115 operates as a diagnosis support information acquisition unit (diagnosis support device) and a contribution information acquisition unit (evaluator). The information acquisition unit 115 inputs the diagnosis support information and contribution information to the page generator 113.

The page generator 113 generates the information page 15. According to the medical care data from the data readout unit 111, the page generator 113 generates the information page 15 in the format of XML or the like. The page generator 113 upon receiving the diagnosis support information or contribution information from the information acquisition unit 115 edits the information page 15 to display the same information. The page generator 113 transmits the information page 15 to the display processor 114 after the editing.

The display processor 114 performs a function for outputting of the information page 15 from the page generator 113. The display processor 114 causes the communication interface 33 to transmit the information page 15 to the client terminal apparatus 12 as a recipient. The client terminal apparatus 12 receiving the information page 15 drives the display panel 34B to display the information page 15. Thus, the doctor can view and read the information page 15, and the diagnosis support information and contribution information in the information page 15. The page generator 113 and the display processor 114 operate as an information output device.

Figure 16:
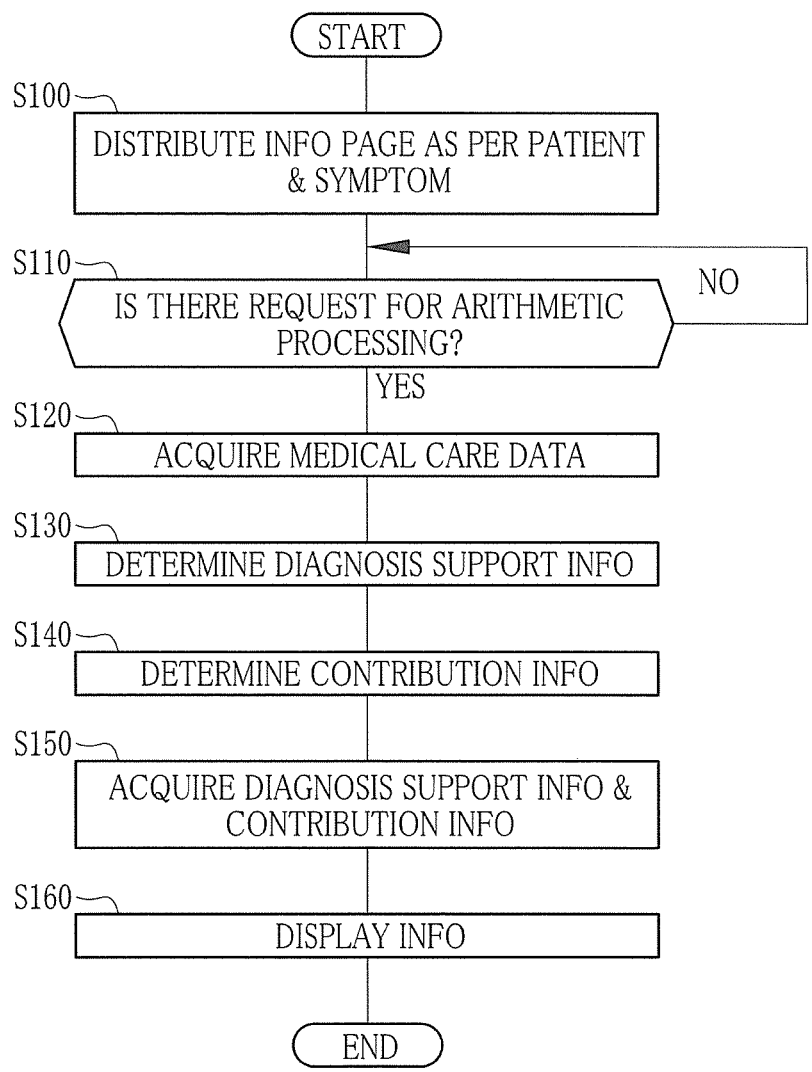
FIG. 16 is a flowchart illustrating operation of a diagnosis support server apparatus.

The operation of the embodiment is described now by referring to FIG. 16. To view medical care data of a patient (patient body) in the information page 15, the client terminal apparatus 12 is set on-line with the diagnosis support server apparatus 11 to transmit a request for information distribution with a designated case ID.

In case the request processor 110 in the diagnosis support server apparatus 11 receives a request for the information distribution with the designated case ID, the data readout unit 111 reads out medical care data of the designated patient. The page generator 113 generates the information page 15 to display the acquired medical care data. The information page 15 is transmitted to the client terminal apparatus 12 by use of the display processor 114 in a step S100. In FIG. 6, the client terminal apparatus 12 causes the display panel 34B to display the information page 15. Thus, the medical care data of the patient can be viewed.

In case the symptom ID is selected in the information page 15, the client terminal apparatus 12 transmits a request for the information distribution with the symptom ID to the diagnosis support server apparatus 11. The diagnosis support server apparatus 11 generates the information page 15 of FIG. 7 with medical care data of the displayed list item according to the selected symptom in the step S100. Thus, the medical care data can be viewed.

In FIG. 7, a list of the diagnosis support programs 101 registered for the respective symptoms is displayed in the message area 54 in the information page 15 after selecting the symptom. In case one of the diagnosis support programs 101 is selected by use of the cursor 42 and the enter button 79 is clicked or pressed, then a request for arithmetic processing with the designated program ID is transmitted to the diagnosis support server apparatus 11.

The diagnosis support server apparatus 11 stands by for receiving the request for the arithmetic processing in a step S110. In case the request processor 110 receives this request, it is judged that the request has occurred with the diagnosis support program 101 (yes in the step S110). Then the request processor 110 transmits a program ID of the designation to the program controller 112. The program controller 112 reads out the diagnosis support program 101 from the storage medium 30A according to the input program ID. An input list item determined by the diagnosis support program 101 being read out is transmitted to the data readout unit 111. The data readout unit 111 reads out medical care data according to the input list item in a step S120. The medical care data is input to the program controller 112.

The program controller 112 runs the diagnosis support program 101 by use of the input medical care data as parameters, to determine diagnosis support information in a step S130. Also, the program controller 112 determines contribution information related to a list item of contribution to determining the diagnosis support information in a step S140. The information acquisition unit 115 acquires the determined diagnosis support information and contribution information from the program controller 112 in a step S150.

The information acquisition unit 115 inputs the diagnosis support information and the contribution information to the page generator 113, which performs display processing of the information page 15 by editing with the diagnosis support information and the contribution information. Then the display processor 114 performs information distribution of the information page 15 to the client terminal apparatus 12. A doctor can view the information page 15 and read the diagnosis support information and the contribution information in a step S160.

The doctor refers to the diagnosis support information for use in the diagnosis. As the contribution information including large contribution list items having contributed to determining the diagnosis support information is displayed, he or she can use the diagnosis support program with reliability according to the system visibility. This is because at least part of a logic flow or process of determination in the diagnosis support program can be clarified although the logic flow or process has been a black box or hidden (invisible) information in a conventional technique. The contribution information becomes information of an index related to the diagnosis support information as a result of the determination. It is possible to provide reliability to the doctor in use of the diagnosis support program owing to the visual evaluation of the diagnosis support information.

In the embodiment, the small contribution list item is included in addition to the large contribution list item in the contribution information, so that the process (logic flow) of the determination can be clearly monitored. The large contribution list item and the small contribution list item constitute all of the list items used in determining the diagnosis support information. It is possible to check all of the used list items by indicating the small contribution list item with the large contribution list item. Traceability for evaluating the diagnosis support information can be ensured as the used list items are data of basis of determining the diagnosis support information.

Displaying large contribution list items makes it possible to avoid practical use of the diagnosis support information assuming that list items with importance to a doctor are included in the small contribution list items, because possibility of a difference from his or her decision is high. In short, the large contribution list items are list items of which relevancy is relatively high in the diagnosis support program, and the small contribution list items are list items of which relevancy is relatively low in the diagnosis support program. It is possible easily to check occurrence of a difference between detected similarity of list items or lesions according to the diagnosis support program and the doctor's detected similarity of list items of lesions in relation to the similar patient case search or image search. Assuming that such a difference is large, it is possible for the doctor practically to decide exclusion of the result of the search from the use.

Also, the numerical values of the medical care data corresponding to the large contribution list items can be readily referred to because the contribution information is displayed in the information page 15.

In the embodiment, the threshold TH for determining large contribution list items is a level 6 according to 10 levels of the scale. However, a threshold TH can be in a different level, which can be higher than a level zero (0). In the setting of the threshold TH of the level zero, small contribution list items are list items without any contribution (unrelated) to determining diagnosis support information. Large contribution list items are list items with a level equal to or more than a level 1, namely, with at least small contribution.

Although both of the large contribution list item and small contribution list item are included in the contribution information in the embodiment, no small contribution list item is required in the present invention. At least the large contribution list item should be included in the contribution information.

In FIGS. 9 and 10, the biochemical test A as a large contribution list item is included in both of the contribution information and the diagnosis support information. It is possible to display this only with the diagnosis support information but not to display the same with the contribution information. It is possible that the number of the list items with the contribution information is higher than that with the diagnosis support information. For this situation, displaying list items in an overlapped manner is avoided with the high number of the displayed list items as contribution information, so that a space for the display can be saved. The number of the list items to be checked is decreased as contribution information, so that efficiency in operation of the check can be high. Even though a list item is not displayed as contribution information, the list item included in the diagnosis support information can be recognized at least in relation to its use for determining the diagnosis support information.

Also, a large contribution list item included in both of the contribution information and diagnosis support information can be indicated with an emphasis in a distinct form. For example, the biochemical test A in FIGS. 9 and 10 can be displayed in a highlighted form in both of the contribution information and diagnosis support information. An example of the distinct form for indicating the large contribution list item can be a special character font of letters different from other alphanumeric information.

Examples of large contribution list items included in both of the contribution information and the diagnosis support information are lesions L1-L3 in the diagnostic image 24 in FIG. 15. It is possible to display distinct information for indicating the inclusion of the large contribution list items in both of the contribution information and the diagnosis support information. For example, diagnosis support information determined by the diagnosis support program 101 (program A3) includes information related to treatment in addition to the similar image, such as treatment with relevancy to the lesion L2. Then the lesion L2 is a large contribution list item included in both of the contribution information and the diagnosis support information.

For example, the lesion L2 is indicated with an emphasis for recognition within the thumbnail image 60 displayed in the imaging area 50D of the record list 50. The emphasis of the lesion L2 among the lesions L1-L3 in the thumbnail image 60 in the imaging area 50D is effective in indicating higher importance of the lesion L2 than the lesions L1 and L3 in obtaining the diagnostic support information.

Second Embodiment

Figure 17:
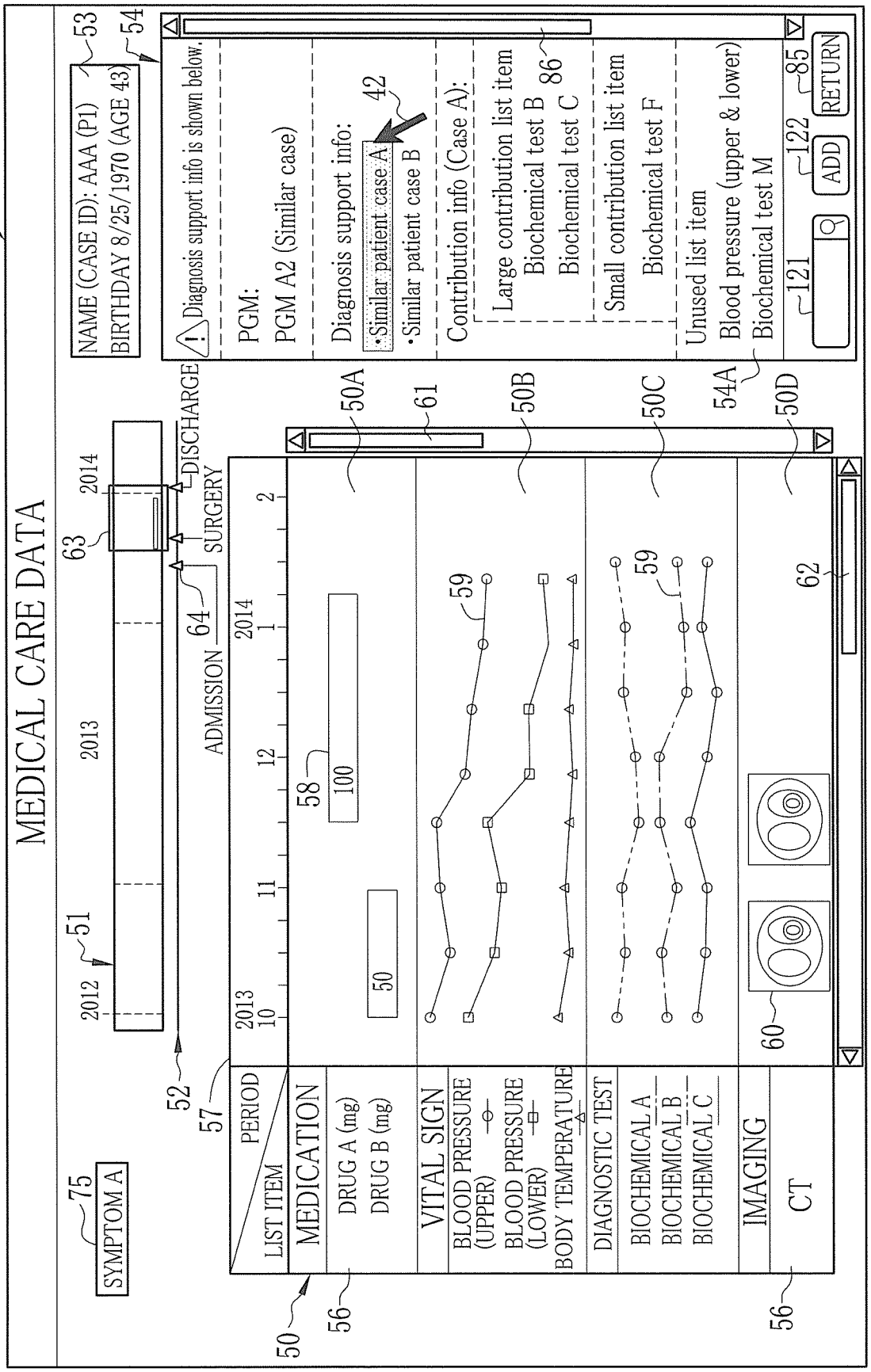
FIG. 17 is a screen view illustrating an information page with unused list items.

In FIG. 17, it is possible in a second embodiment to display information related to unused list items without use for determining the diagnosis support information in the information page 15 in addition to the contribution information. The unused list items are list items not included in input list items of the diagnosis support information among medical care data of the patient. Displaying the information of the unused list items is effective in clarifying list items not having been used for determining the diagnosis support information. Assuming that a list item which a doctor judges to be important is included in the unused list items, it is possible not to use the diagnosis support information practically because of a difference from his or her decision of the diagnosis.

A search box 121 and an add button 122 can be provided for displaying the unused list item. The search box 121 is a GUI tool for searching an unused list item with a query or keyword. For example, a query can be input to check whether a list item required by a doctor is included in unused list items. The effect of the use of the search box 121 is easily detecting required list items typically in case the unused list items are very numerous, for example, in case information of DNA (deoxyribonucleic acid) or other genetic information is included in the list items.

Furthermore, it is possible to add one of the unused list items as a new input list item by input action of designation at the subsequent time of determining diagnosis support information. The add button 122 is used for adding the unused list item as a new input list item. One of the unused list items in the information of the unused list items is pointed by use of the cursor 42. The add button 122 is pressed or clicked to add the list item as new list item.

Thus, the additional function makes it possible easily to add required list items even among unused list items. In FIGS. 12 and 13, optional list items are predetermined in the input list items in the diagnosis support programs 101. For example, the added input list items are added as optional list items.

Also, a function for search can be added with the search box 121 for searching used list items having a large contribution list item and small contribution list item included in the contribution information, in addition to or in place of searching unused list items. The search box 121 can be two boxes for the unused list items and used list items, or also can be a single box selectively changed over between the list items.

The used list item which a doctor wishes to check can be easily searched owing to the search function. The search function is effective specially in case the number of the list items is high in the same manner as the unused list items. Furthermore, it is possible to allocate a tag to a frequently searched list item as an important list item requiring check, and to display the result of the search at a higher display rank in the information page 15 irrespective of the contribution value (relevancy score).

Third Embodiment

Figure 18:
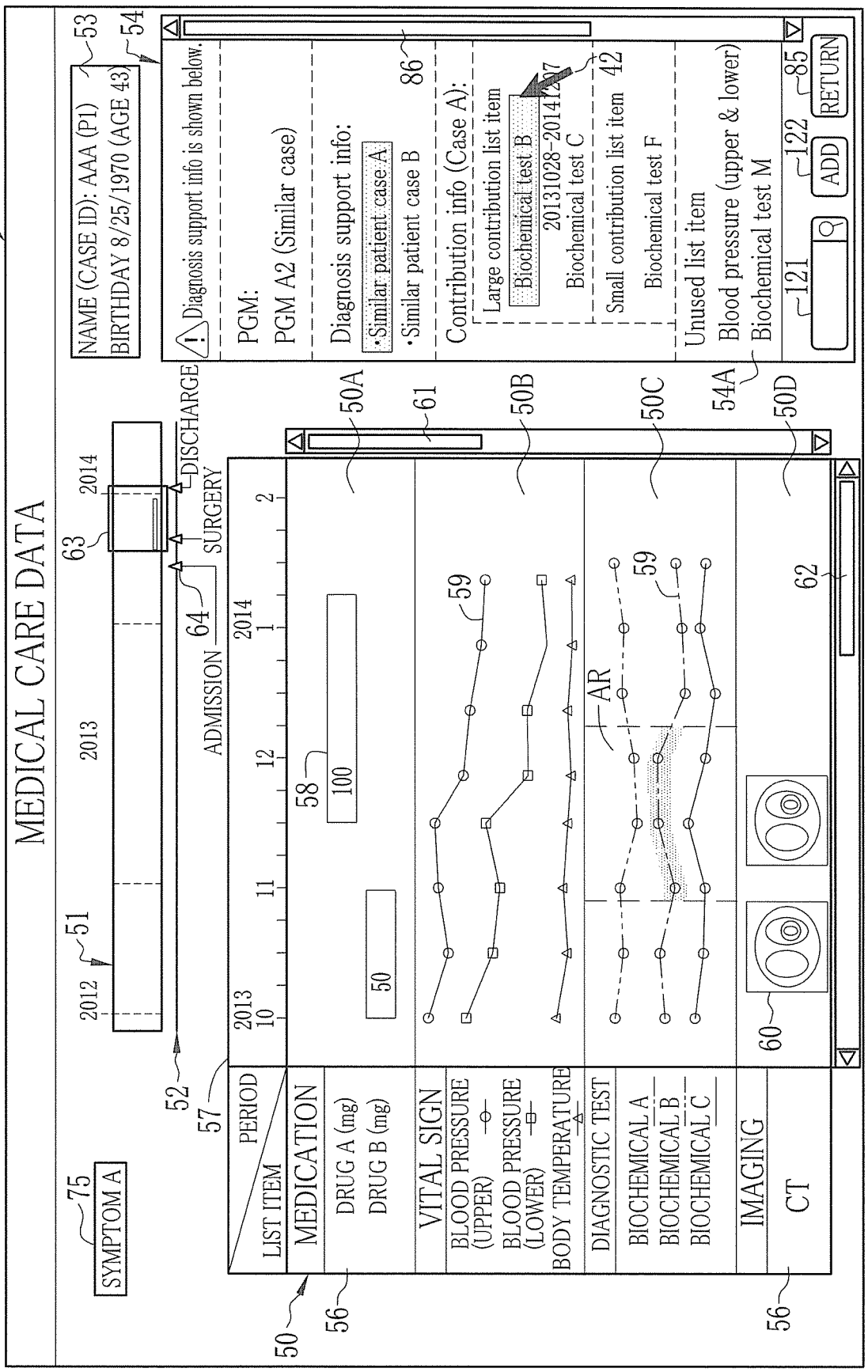
FIG. 18 is a screen view illustrating an information page with information of a period.

In FIG. 18, information of a period of the time sequential data used in determining the diagnosis support information can be included in the contribution information, for example, in case medical care data of input list items such as the line graphs 59 of the test values is the time sequential data for changeable numerical values. In short, information of a period of the use is displayed assuming that part of the period is used in the time sequential data while the diagnosis support program 101 is run in the program controller 112.

In the embodiment, the time sequential data of test values of the biochemical tests B and C and the like is used as input list items. Data of the test values in a period from 20131028 until 20141207 is used for determining the diagnosis support information among the time sequential data of the biochemical test B with the line graphs 59. In case the biochemical test B is specified by press or click with the cursor 42 in the contribution information in the message area 54, information of the period "20131028-20141207" is displayed beside the biochemical test B.

Also, information of the period is displayed in the record list 50 in response to the designating operation. In the test area 50C, one of the line graphs 59 of the biochemical test B is displayed with an emphasis for the used period as hatched in the drawing. It is possible to indicate the entirety of a particular area AR surrounded by the dotted lines for the used period with an emphasis distinct from remaining portions within the test area 50C, without only emphasizing the line graph 59 of the biochemical test B.

In case there is a large change in the measurement value according to the period in the time sequential data, selection of one of the periods for use is very relevant to determining the diagnosis support information. In the present embodiment, indicating the information of the period used in the diagnosis support information in the time sequential data makes it possible to review the diagnosis support information precisely as a result of the determination according to the test value of the period. The process (logic flow) of determination in the diagnosis support program can be clarified with the system visibility in an ensured manner.

Fourth Embodiment

Figure 19:
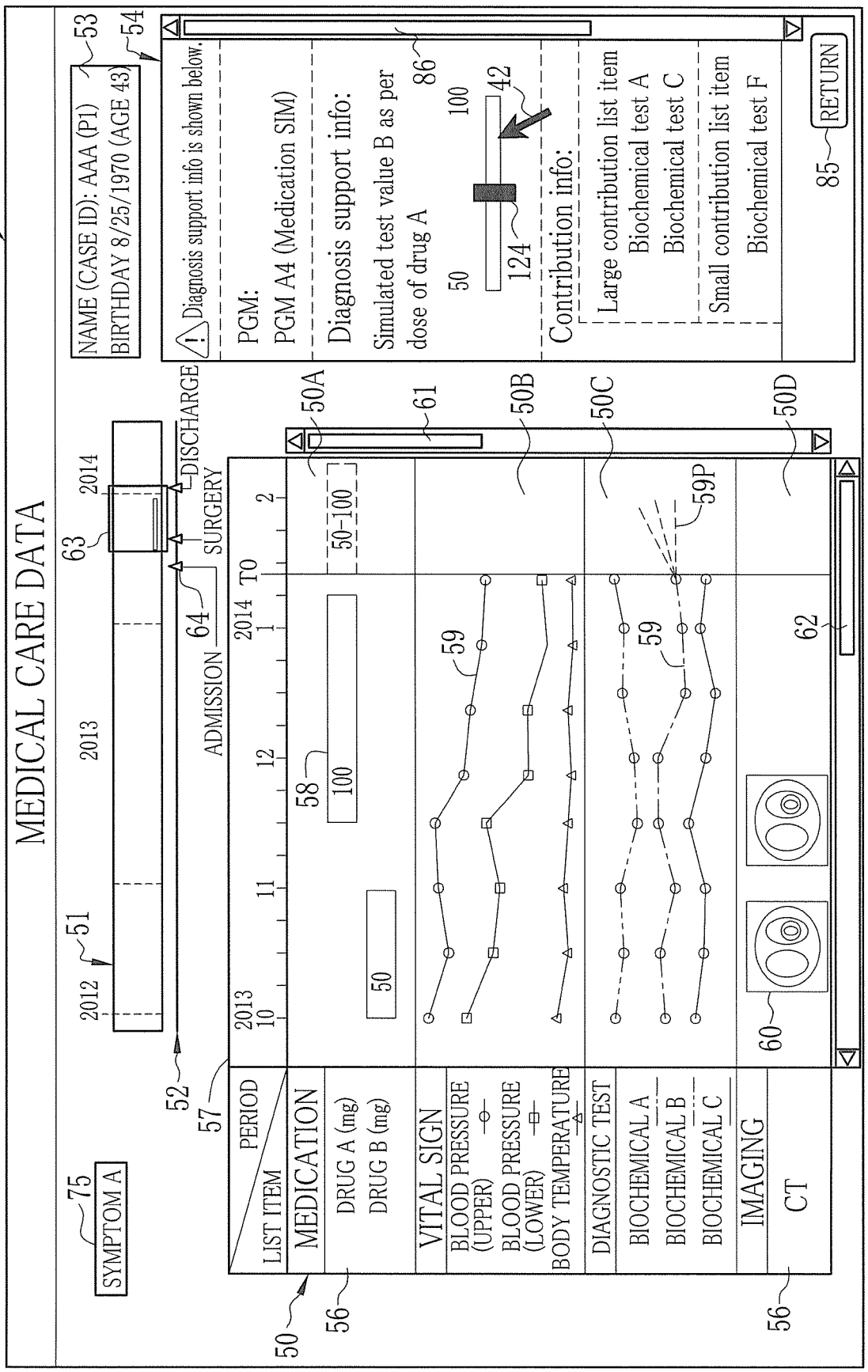
FIG. 19 is a screen view illustrating an information page with a result of simulated drug administration.

In FIGS. 19 and 20, a program A4 as the diagnosis support program 101 is used for simulation of the drug administration (SIM). The program A4 determines a simulation result of a test value B for the diagnosis support information according to changes in the dose of the drug A, according to a modeling polynomial equation (1) indicated later, which is obtained by use of multiple linear regression as an analysis included in multivariate analyses. The test value B is a test value of the biochemical test B.

Let the dose of the drug A be changed in a range of 50-100 in the medication area 50A in FIG. 19. A result of simulation is obtained in relation to changes in the test value B at the time no earlier than the present time T0 in the test area 50C. An estimated value 59P is indicated on the line graph 59 of the test value B for the result of the simulation.

A slider 124 is disposed in the message area 54 for changing a designated dose of the drug administration. Sliding the slider 124 by use of the cursor 42 designates the dose between 50 and 100. A change in the dose changes the estimated value 59P.

In FIG. 20, biochemical tests A, C and D are set in the program A4 as input list items. The test value B as an estimated value is obtained as a response variable according to the following polynomial equation (1) in which test values of the biochemical tests A, C and D are plural explanatory variables.

Test value $B = \alpha \times$ test value $A + \gamma \times$ test value $C + \delta \times$ test value $D + \ldots$    Equation (1):

For coefficients of $\alpha$, $\gamma$, $\delta$ and so on of the respective terms in the polynomial equation, plural coefficients according to the dose are determined, such as $\alpha 1$, $\alpha 2$, $\alpha 3$, ..., $\gamma 1$, $\gamma 2$, $\gamma 3$, ..., $\delta 1$, $\delta 2$, $\delta 3$ and so on. In case the slider 124 is operated in the information page 15, those coefficients change. Test values are substituted for test values A, C and D as explanatory variables by way of predicted values in a period on or after the present time T0. The test value B according to the dose of the drug administration is obtained by performing arithmetic processing with those values as parameters. The predicted values are input as time sequential data at plural time points on or after the present time T0. Thus, the test value B as the predicted value is displayed as the time sequential data at the plural time points in the manner of the line graph 59, not a predicted value only at one time point.

For the contribution value (relevancy score), a t-value of each term in the polynomial equation (1) is used. The t-value is an amount of relevancy of an explanatory variable to a response variable (objective variable) in multiple linear regression. The relevancy is higher according to highness of the t-value. The program controller 112 outputs the t-value of each term of the test values A, C and D as explanatory variables in the polynomial equation (1). The contribution information is obtained from the contribution value after normalizing the t-value. In the embodiment, the t-value of the test value A is the highest. The t-value of the test value C is the second highest. As the contribution value is higher than the threshold TH, the biochemical tests A and C are the large contribution list items. Those are arranged in the display sequence of the highness of the contribution information, namely A and then C.

It is possible for the doctor to determine a suitable dose by use of the simulation. For example, he or she can practically decide that the dose should be decreased to minimize influence of adverse effect of the drug in case no large change occurs in the test value even upon an increase in the dose.

Also, plural list items can be predicted. For example, one of the list items to be predicted is a first test value of interest which should be lowered by administering a drug. A second one of the list items is a second test value for which adverse effect may occur after drug administration. For this case, polynomial equations for determining predicted values of the list items are used. A change in the first test value of interest with a change in the drug administration, and a change in the adverse effect are simulated by use of the polynomial equations, and results of the simulation are displayed. Thus, it is possible to determine dose of the drug by checking and considering the changes in the adverse effect.

In the above embodiments, the contribution information is displayed in the information page 15 for provision to a user. However, a data file including the contribution information can be distributed to the user by information distribution without display in the information page 15, for the purpose of provision to the user. To this end, a file output device is provided as an information output device.

In the embodiments, the input list items of the diagnosis support programs 101 have been described as predetermined list items for each program. However, it is possible for a user or doctor manually to designate input list items at the time of determining the diagnosis support information. Thus, the determination of the diagnosis support information can be ensured on the basis of the medical care data of the tests of interest with high importance to the user. Also, it is possible in the similar image search to designate a lesion for priority in the use of the lesion of a particular interest to the user.

In the above embodiments, the program controller 112 is provided in the diagnosis support server apparatus 11. However, the program controller 112 can be provided in a separate second server. The diagnosis support server apparatus 11 can only acquire the diagnosis support information and contribution information output by the program controller 112. For this structure, the diagnosis support program 101 is run by the second server, of which a result is transmitted to the diagnosis support server apparatus 11. The diagnosis support program 101 acquires medical care data, diagnostic images and the like from an EMR or the PACS, and determines an input list item for use. Although the diagnosis support server apparatus 11 is not relevant to determining the contribution information, the diagnosis support server apparatus 11 acquires the diagnosis support information and contribution information from the second server after arithmetic processing of the diagnosis support information and contribution information by the diagnosis support program 101 in the second server. The diagnosis support server apparatus 11 generates the information page 15 upon addition of the diagnosis support information and contribution information being acquired.

It is preferable to standardize the communication protocol, data format and other settings for communication for the purpose of communication between the diagnosis support server apparatus 11 and other server apparatuses so as to acquire the contribution information and diagnosis support information from the other server apparatus. This structure of the standardization is effective in increasing suitability for connection with the other server apparatuses in which the diagnosis support program 101 according to future technical development may be run.

The diagnosis support programs are not limited to the above embodiments. Other diagnosis support programs with further functions can be used. There are various sets of diagnosis support information and contribution information with differences according to the functions.

In the above embodiments, one computer constituting the diagnosis support server apparatus 11 is used as the diagnosis support apparatus. However, various functions of the diagnosis support apparatus can be performed discretely in plural computers. For example, the diagnosis support server apparatus 11 can be constituted by a plurality of server computers as separate hardware units for the purpose of enhancing performance of processing and raising reliability. Hardware construction of the computers can be suitably modified according to required performance, for example, ability of processing, safety, reliability and the like.

In the above embodiments, the diagnosis support server apparatus 11 is the diagnosis support apparatus for information distribution of the information page 15 with the application service. However, the client terminal apparatus 12 itself can be used to perform a function of a diagnosis support apparatus. To this end, the CPU in the client terminal apparatus 12 operates with the components of the request processor 110, the data readout unit 111, the information acquisition unit 115, the page generator 113 and the display processor 114. The request processor 110 receives an input action from the input device 35B by use of the control page displayed in the display panel 34B of the client terminal apparatus 12. The display processor 114 outputs the information page 15 to the display panel 34B of the client terminal apparatus 12.

The information acquisition unit 115 in the client terminal apparatus 12 acquires the contribution information and diagnosis support information from the second server apparatus running the diagnosis support program 101. Assuming that the client terminal apparatus 12 includes the program controller 112, the information acquisition unit 115 receives the contribution information and diagnosis support information from the program controller 112. Also, either the contribution information or the diagnosis support information can be acquired from the second server apparatus. For example, a search result of the similar image as diagnosis support information can be acquired from the second server apparatus in the case of the similar image search. Contribution information can be determined in the client terminal apparatus 12 according to the information from the second server apparatus, for example, information of the similarity score in the similar image search.

In the above embodiments, the diagnosis support system 10 is installed in the hospital facility or medical facility. However, the diagnosis support server apparatus 11 can be used in a shared form remotely between a plurality of hospital facilities.

In the above embodiments, the client terminal apparatus 12 in one hospital facility is connected to the diagnosis support server apparatus 11 communicably by use of the LAN 14 or other network. The diagnosis support server apparatus 11 provides an application service of diagnosis support in response to a request from the client terminal apparatus 12. To use the application service in the plural hospital facilities, the diagnosis support server apparatus 11 is set on-line with the plural client terminal apparatuses 12 positioned in the hospital facilities by use of the wide area network (WAN), such as the Internet, public communication network and the like. Requests from the client terminal apparatuses 12 of the hospital facilities are received by the diagnosis support server apparatus 11 with the WAN, to provide the application service of the diagnosis support to the client terminal apparatus 12. Note that information security should be established for use of the WAN, for example, the Virtual Private Network (VPN) or Hypertext Transfer Protocol Secure (HTTPS) can be preferably used as communication protocol of a high level of security. A location and manager of the diagnosis support server apparatus 11 can be a data center as a company (service provider) separate from the hospital facilities, but can be a particular one of the hospital facilities.

The present invention is not limited to the above embodiments. Various features of the embodiments and variants of the invention can be combined with each other suitably.

Also, the computer-executable program and a storage medium for storing the computer-executable program are included in the scope of the present invention.

According to one embodiment mode of the invention, a user interface for diagnosis support for diagnosis of a patient body is provided, and includes a diagnosis support information area for displaying diagnosis support information determined for use in reference for the diagnosis by running a diagnosis support program according to plural input list items related to medical care data of the patient body. A contribution information area displays contribution information, generated by comparing a contribution value of contribution of the input list items to determining the diagnosis support information with a predetermined threshold, and related to at least one large contribution list item of which the contribution value is equal to or more than the threshold.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A diagnosis support apparatus for diagnosis of a patient body, comprising:
   a request processor, receiving a request including query information;
   a program controller, obtaining input list items according to the query information;
   a data readout unit, obtaining medical care data corresponding to the input list items according to the query information from a database;
   an information acquisition unit, acquiring diagnosis support information determined by the program controller for use in reference for said diagnosis, and acquiring contribution information generated by the program controller, wherein the contribution information represents a level of contribution of the input list items that contributes in determining the diagnosis support information; and
   an information output device for providing said diagnosis support information and said contribution information,
   wherein the program controller loads a diagnosis support program from a storage memory, performs arithmetic process by running the diagnosis support program using the input list item related to the medical care data of said patient body to determine the diagnosis support information, and generates the contribution information by comparing a contribution value corresponding to the input list items used for determining the diagnosis support information with a predetermined threshold.

2. A diagnosis support apparatus as defined in claim 1, wherein said information output device performs display processing to display said diagnosis support information and said contribution information in an information page for displaying said medical care data.

3. A diagnosis support apparatus as defined in claim 2, wherein said information acquisition unit acquires information of a small contribution list item of which the contribution value to said determined diagnosis support information is less than said predetermined threshold among said input list items, and acquires information of a large contribution list item of which the contribution value to said determined diagnosis support information is less than said predetermined threshold among said input list items; and said information output device displays said large contribution list item and said small contribution list item distinctly from one another.

4. A diagnosis support apparatus as defined in claim 2, wherein said information page displays at least one large contribution list item in a display sequence of highness of said contribution value, wherein said at least one large contribution list item is the at least one of the input list items which has the contribution value equal to or more than said predetermined threshold.

5. A diagnosis support apparatus as defined in claim 2, wherein in case one of at least one large contribution list item is specified in said information page, said medical care data corresponding to said specified large contribution list item is displayed, wherein said at least one large contribution list item is the at least one of the input list items which has the contribution value equal to or more than said predetermined threshold.

6. A diagnosis support apparatus as defined in claim 2, wherein in case plural sets of said diagnosis support information are displayed in said information page and one of said sets is specified, then at least one large contribution list item related to a specified set is displayed wherein said at least one large contribution list item is the at least one of the input list items which has the contribution value equal to or more than said predetermined threshold.

7. A diagnosis support apparatus as defined in claim 2, wherein said medical care data corresponding to said input list items is time sequential data for changes in a value with time, and said information page displays information of a period of said time sequential data used for determining said diagnosis support information.

8. A diagnosis support apparatus as defined in claim 7, wherein said information of said period is displayed with an emphasis in correspondence with at least one large contribution list item, wherein said at least one large contribution list item is the at least one of the input list items which has the contribution value equal to or more than said predetermined threshold.

9. A diagnosis support apparatus as defined in claim 2, wherein assuming that there is an unused list item unused in determining said diagnosis support information among said input list items, information of said unused list item is displayed in said information page.

10. A diagnosis support apparatus as defined in claim 9, wherein said unused list item is additionally specifiable as an input list item for subsequently determining said diagnosis support information.

11. A diagnosis support apparatus as defined in claim 1, wherein said diagnosis support program produces said diagnosis support information by simulation with a polynomial equation, and at least one large contribution list item is a list item corresponding to at least one of plural explanatory variables in said polynomial equation, wherein said at least one large contribution list is the at least one of the input list items which has the contribution value equal to or more than said predetermined threshold.

12. A diagnosis support apparatus as defined in claim 1, wherein a function of said diagnosis support program includes a function of at least one of suggesting a drug, searching a similar patient case, searching a similar image, and simulating administration of a drug.

13. A diagnosis support apparatus as defined in claim 1, wherein said input list items include at least one of list items related to medication, a vital sign, a diagnostic test and imaging.

14. A diagnosis support method for diagnosis of a patient body, comprising steps of:
- receiving a request including query information by a request processor;
- obtaining input list items according to the query information by a program controller;
- obtaining medical care data corresponding to the input list items according to the query information from a database by a data readout unit;
- acquiring diagnosis support information determined by the program controller for use in reference for said diagnosis;
- acquiring contribution information, wherein the contribution information represents a level of contribution of the input list items that contributes in determining the diagnosis support information, wherein the program controller loads a diagnosis support program from a storage memory, performs arithmetic process by running the diagnosis support program using the input list item related to the medical care data of said patient body to determine a diagnosis support information, and generating the contribution information by comparing a contribution value corresponding to the input list items used for determining the diagnosis support information with a predetermined threshold;
- providing said diagnosis support information and said contribution information.

15. A non-transitory computer readable medium for storing a computer-executable program enabling execution of computer instructions to perform operations for diagnosis support for diagnosis of a patient body, said operations comprising:
- receiving a request including query information;
- obtaining input list items according to the query information;
- obtaining medical care data corresponding to the input list items according to the query information from a database;
- acquiring diagnosis support information determined for use in reference for said diagnosis;
- acquiring contribution information, wherein the contribution information represents a level of contribution of the input list items that contributes in determining the diagnosis support information, wherein arithmetic process is performed by running a diagnosis support program using the input list item related to the medical care data of said patient body to determine a diagnosis support information, and the contribution information is generated by comparing a contribution value corresponding to the input list items used for determining the diagnosis support information with a predetermined threshold; and
- providing said diagnosis support information and said contribution information.

* * * * *